United States Patent [19]
Patierno et al.

[11] Patent Number: 6,054,320
[45] Date of Patent: Apr. 25, 2000

[54] KIT FOR INDENTIFYING PROSTATIC INTRAEPITHELIAL NEOPLASIA (PIN)

[75] Inventors: Steven R. Patierno, Falls Church, Va.; Michael J. Manyak, Chevy Chase, Md.

[73] Assignee: George Washington University, Washington, D.C.

[21] Appl. No.: 08/966,196

[22] Filed: Nov. 7, 1997

Related U.S. Application Data

[60] Division of application No. 08/658,796, Jun. 5, 1996, Pat. No. 5,935,860, which is a continuation-in-part of application No. 08/486,203, Jun. 7, 1995, Pat. No. 5,830,640, which is a continuation-in-part of application No. 08/400,084, Mar. 7, 1995, Pat. No. 5,696,092.

[51] Int. Cl.[7] .................................................. G03G 15/04
[52] U.S. Cl. ............................................................ 436/64
[58] Field of Search .................................................. 436/64

[56] References Cited

U.S. PATENT DOCUMENTS

| | | | |
|---|---|---|---|
| 5,266,562 | 11/1993 | Mukherjee et al. | 514/14 |
| 5,284,827 | 2/1994 | Maione et al. | 530/380 |
| 5,359,078 | 10/1994 | Kohn et al. | 548/265.8 |

FOREIGN PATENT DOCUMENTS

| | | |
|---|---|---|
| 91/07187 | 5/1991 | WIPO . |

OTHER PUBLICATIONS

Medline 82053036, abstract of Snead, J of Biological Chemistry, 1981, 256(22), pp. 11911–11916.
Manyak et al., J. Urology 140:176–182 (1988).
Broers et al., Laboratory Investigation 66(3): 337–346 (1992).
Miyamoto et al., J. Urology 149: 1015–1019 (May 1993).
Jensen et al., Int. J. Cancer 58: 629–637 (1994).
Linnoila et al., A.J.C.P. 97(2): 223–243 (Feb. 1992).
Peri et al., J. Clinical Inv. 92: 2099–2109 (Nov. 1993).
Morgan et al., Annu. Rev. Biochem. 62: 191–217 (1993).
Tolstoshev, Annu. Rev. Pharmocol. Toxicol. 32: 573–96 (1993).
Hill, R.R., Chapter 11, Metastasis, pp. 178–195 in *The Basic Science of Oncology*, Tannock et al., Eds., McGraw–Hill, N.Y. (1992).
Aznavoorian et al., *Cancer,* 71: 1368–83 (1993).
Singh et al., *BBA,* 950: 329–337 (1988).
Miele et al., *Endocrine Reviews,* 8: 474–90 (1987).
Nieto et al., *Arch. Biochem. Biophys.,* 180: 82–92 (1977).
Mantile et al., *J. Biol. Chem.,* 268: 20343–20351 (1993).
Miele et al., *J. Biol. Chem.,* 265: 6427–35 (1990).
Sambrook et al., Molecular Cloning: A Laboratory Manual, 2nd Ed., Cold Spring Harbor Laboratory Press, Cold Spring Harbor, N.Y. (1989).
Arcone et al., *Eur. J. Biochem.,* 211: 347–55 (1993).
Cirino et al., *British J. Pharmacol.,* 108:573–4 (1993).
Bastian et al., *J. Invest. Dermatol.,* 101:359–63 (1993).
Monoclonal Antibodies—Production, Engineering and Clinical Applications, Ritter et al., Eds., Cambridge University Press, Cambridge, UK (1995).
Merk Index, 11th Ed., Budavari et al., Eds., Merk & Co., Inc. Rahway, N.J. (1989).
Goodman and Gilman's: The Pharmacological Bases of Therapeutics, 8th Ed., Gilman et al., Eds., Pergamon Press (1990).
Remington's Pharmaceutical Sciences, 17th Ed., Mack Publishing Co., Easton, PA (1990).
Cancer Therapy With Radiolabeled Antibodies, D.M. Goldenberg, Ed., CRC Press, Boca Raton, FL (1995).
Stone et al., *Int. J. Cancer,* 21: 274–281 (1978).
Horoszewicz et al., *Cancer Res.,* 43: 1809–18 (1983).
Kaighn et al., *Invent. Urol.,* 17: 16–23 (1979).
Hzumi et al., *J. Urology,* 137: 1304–1306 (1987).
Albini et al., *Cancer Research,* 47: 3239–3245 (1987).
Leyton et al., *Cancer Research,* 54: 3696–3699 (1994).
Frandson et al., *Fibrinolysis,* 6 (Supp. 4): 71–76 (1992).
Manyak et al., *J. Urology,* 151: 368A (1994).
Cerbóon et al., *J. steroid Biochem.,* 36: 1–6 (1990).
López de Haro et al., *FEBS Letters,* 232: 351–353 (1988).
Aumuller et al., *Histochemistry,* 83: 413–417 (1985).
Tibes et al., *Expert Opin. Invest. Drugs,* 6: 279–298 (1997).
Dannhorn et al., *J. Immunol. Meth.,* 119: 223–230 (1989).
Osband et al., *Immunology Today,* 11: 193–195 (1990).
Mayer et al., *Expert Opin. Invest. Drugs,* 5: 535–554 (1996).
Leyton et al., *Proc. Amer. Assoc. Canc. Res.* 35: 280 (1994).

*Primary Examiner*—D. Margaret Seaman
*Attorney, Agent, or Firm*—Nath & Associates; Gary M. Nath; Todd L. Juneau

[57] ABSTRACT

The invention relates to methods for identifying prostatic intraepithelial neoplasia, methods for determining metastatic potential of tumors, and to methods and compositions for inhibiting or preventing metastasis of cancers. In one aspect, the invention provides a method to determine metastatic potential of tumors, particularly prostatic tumors. In another aspect, the invention provides a method of identifying prostate cancer associated conditions, particularly prostatic intraepithelial neoplasia. In these regards, the invention relates to determining protein or mRNA of effectors of arachidonic acid release, particularly uteroglobin protein or mRNA, to identify intermediate conditions such as PIN or to gauge metastatic potential of prostatic tumors. The invention also relates to methods and compositions that prevent or inhibit metastasis of cancers. In this regard, the invention particularly relates to methods and compositions that inhibit arachidonic acid, those that inhibit phospholipase $A_2$. More particularly in this regard, the invention relates to uteroglobin or muteins, peptide analogs or mimetics of uteroglobin and lipocortins or muteins, peptide analogs, or mimetics of lipocortins that inhibit metastasis. Especially it relates to methods and compositions in which uteroglobins, particularly human uteroglobins, inhibit or prevent metastasis of cancer, particularly prostatic cancer.

9 Claims, 5 Drawing Sheets

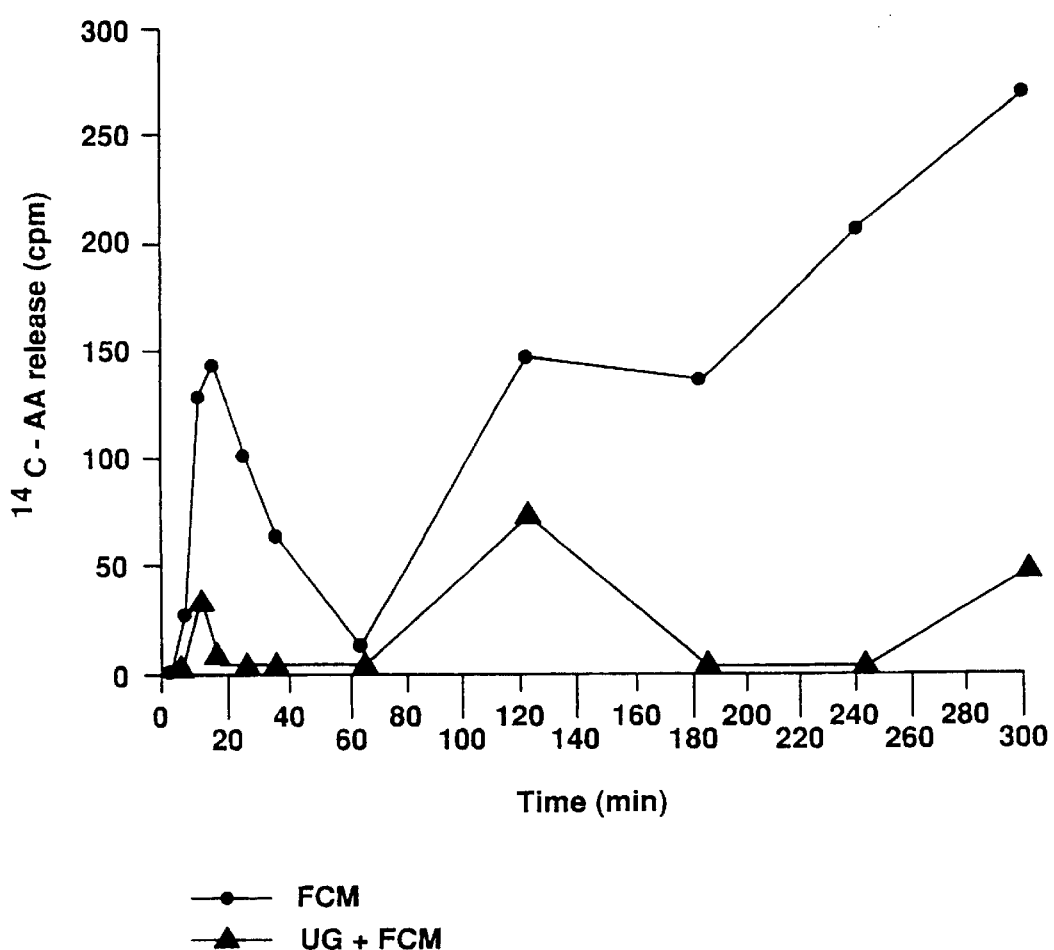

KIT FOR INDENTIFYING PROSTATIC INTRAEPITHELIAL NEOPLASIA (PIN)

This application is a division of U.S. patent application Ser. No. 08/658,796, filed Jun. 5, 1996, now U.S. Pat. No. 5,935,860, which is a continuation-in-part of U.S. patent application Ser. No. 08/486,203, filed Jun. 7, 1995, now U.S. Pat. No. 5,830,640, which is a continuation-in-part of U.S. patent application Ser. No. 08/400,084, filed on Mar. 7, 1995, which is U.S. Pat. No. 5,696,092, the entirety of both of which are incorporated by reference herein.

The present invention relates to methods and compositions that provide for the diagnosis and treatment of prostatic intraepithelial neoplasia. A particular aspect of the invention relates to methods and compositions containing compounds which inhibit phospholipase $A_2$, particularly those that contain uteroglobin, uteroglobin muteins, uteroglobin mimetics, peptide analogs of uteroglobins, lipocortins, lipocortin muteins and peptide analogs of lipocortins. Further compositions of the invention include other types of active ingredients in combination with those described above.

The present invention also relates to methods for gauging the metastatic potential of tumors of epithelial cell origin by determining an effector of arachidonic acid release in cells of a tumor-containing tissue. This aspect of the invention particularly relates to determining uteroglobin protein or mRNA in cells of a biopsy sample to determine metastatic potential of a prostatic tumor.

The present invention further relates to methods and compositions that prevent or inhibit metastases of cancers of epithelial cell origin, especially human prostate cancers. A particular aspect of the invention relates to methods and compositions that inhibit arachidonic acid release in cells of these cancers and inhibit or prevent metastasis. In one aspect in this regard, the invention particularly relates to methods and compositions that inhibit phospholipase $A_2$ that mediates arachidonic acid release in the cancer cells. Compositions of the invention also particularly include those that contain uteroglobin, uteroglobin muteins, peptide analogs of uteroglobins, lipocortins, lipocortin muteins and peptide analogs of lipocortins that inhibit arachidonic acid release by cancer cells. Further useful in this regard are mimetic compounds, particularly uteroglobin and lipocortin mimetics. In this regard, the invention relates especially to compositions that contain mimetics of uteroglobin, particularly of human uteroglobin. Further compositions of the invention include other types of active ingredients in combination with those that inhibit arachidonic acid release.

The invention also particularly relates to methods to prevent or inhibit metastases of human cancers of epithelial cell origin by administering the foregoing compositions. Especially in this regard the invention relates to methods using human uteroglobin to inhibit or prevent metastasis of human prostate cancers. Further, this aspect of the invention may be accomplished by genetic therapy.

Methods and compositions of the invention may be used by themselves and with other treatment modalities.

BACKGROUND OF THE INVENTION

Cancers develop from uncontrolled multiplication of cells. All cancers are life threatening. Even when cancer does not result in death, it is permanently debilitating, not only to the patient, but also to family, friends and co-workers. Too often, moreover, cancers prove fatal. The personal and public loss from this cluster of diseases, which cause a significant fraction of all premature deaths, is beyond estimation.

Although effective treatment modalities have been developed in a few cases, many cancers remain refractory to currently available therapies. Particularly difficult to treat are metastatic cancers. These cancers pose the highest risk to patients and, for optimal prognosis, often must be treated by aggressive methods that present increased risks of deleterious side-effects. Therefore, there is a great need for methods that accurately distinguish those tumors that are likely to metastasize from those that are unlikely to do so. Furthermore, methods for treating metastatic cancers often are inadequate, and there also is a clear need for improved anti-metastatic agents and methods to treat metastatic cancers.

Similarly, there is a great need for methods that accurately identify cells that are associated with prostate cancer, such as those found in prostatic intraepithelial neoplasia (PIN). Current diagnostic methods are inadequate to differentiate between PIN and normal cells. Thus, there is a clear need for improved early detection of PIN which may allow for early diagnosis, prognosis, and treatment of cancer.

Metastatic cancers originate from a primary tumor. Metastasis of the primary tumor produces secondary tumors and disseminated cancer. It is well known that both primary and secondary tumors shed large numbers of cells. The shed cells can spread through the body. For instance, a primary tumor may damage the surrounding lymph or circulatory vessels, allowing entry of shed cells into the lymph or circulatory systems, and hastening their spread in the body. Moreover, shedding of cells by cancerous tumors increases during surgery and radiotherapy.

Most shed cells do not form new tumors. To do so such cells must surmount a series of physical and physiological barriers. In fact, a series of distinct events must occur for metastasis to occur. The primary tumor physically must (i) invade interstitial space of the primary tissue. In particular, it must (ii) penetrate the basement membrane of the tissue. For most metastases the tumor must damage the endothelial cell wall of lymphatic or vascular vessels to provide access to shed cells. Cells that enter the lymph or blood must (iii) survive hemodynamic stress and host defenses in the circulation and, furthermore, (iv) the cells must lodge at a new site in the circulatory system, a process that apparently involves aggregated platelets. A cell then must (v) extravasate out of the vessel into the interstitial is space. Finally, it must (vi) invade the interstitial space of the secondary organ and proliferate in the new location. Although the process of metastasis is physiologically complex, the overall pattern of metastasis is general to many types of cancers.

The metastatic process also clearly involves complex intracellular mechanisms that alter cancerous cells and their interactions with surrounding cells and tissues. For instance, cancerous cells are characterized by aberrant expression of adhesion proteins, enzymes that degrade matrix components, autocrine factors, ligand-responsive receptors, factors of angiogenesis and prostaglandins, to name a few. In particular, the signaling pathways that initiate tumor cell migration are among the least understood aspects of invasion and metastasis. Currently, it is thought that proliferation of many cancerous cells depends upon specific ligand-receptor interactions. Thus far, however, it has not been possible to use this paradigm, or other concepts of the underlying mechanisms of metastasis, to develop a therapy that prevents or effectively inhibits metastasis of metastatic cancers.

The complexity of the processes involved in metastasis, and the lack of understanding of underlying molecular mechanisms, have made it particularly difficult, in some cases, to distinguish tumors that are likely to metastasize from those that are unlikely to do so. The inability to discern the metastatic potential of tumors precludes accurate prognosis and leads, inevitably, to the therapeutic intervention that either is too aggressive or insufficiently aggressive. Furthermore, for all types of cancers it has been difficult or impossible, thus far, to develop treatments that inhibit or prevent the spread of metastatic tumors. Clearly, there remains a great need for methods to accurately determine the metastatic potential of tumors and for effective antimetastatic compositions and methods.

SUMMARY OF THE INVENTION

It is therefore an object of the present invention to provide methods and compositions for differentiating PIN from normal prostate epithelia.

It is also an object of the present invention to provide methods and compositions for early detection of prostate cancer and cells associated with prostate cancer.

It is another object of the present invention to provide methods for inhibiting or preventing metastasis.

It is another object of the present invention to provide compositions for inhibiting or preventing metastasis.

In accomplishing the foregoing objects, there has been provided, in accordance with one aspect of the present invention, a method for identifying prostatic intraepithelial neoplasia, comprising the step of administering to an organism suffering from a cancer of epithelial cell origin a compound that inhibits arachidonic acid release by cells of the cancer by a route and in an amount and manner effective to identify the prostatic intraepithelial neoplasia.

Another method of the present invention is directed to a diagnostic kit for the detection of prostatic intraepithelial neoplasia in a biopsy sample, the kit comprising: a first reagent that binds specifically to an effector of arachidonic acid release in cells in a biopsy sample prepared for determination of the effector, and a second reagent for detectably labelling the primary binding reagent bound specifically to cells in the biopsy sample, wherein the determination of the effector is diagnostic of prostatic intraepithelial neoplasia.

In certain preferred embodiments of the kits of the invention, the effector is an inhibitor of $PLA_2$, among which uteroglobin is particularly preferred.

In certain further preferred embodiments of the this aspect of the invention, the first reagent is an antibody. In these embodiments, the determination would occur where uteroglobin-antibody staining would indicate normal prostate epithelia if strong staining occurred, prostatic intraepithelial neoplasia if weak staining occurred, and cancer if no signal occurred.

Additional preferred embodiments of this aspect of the invention are those in which the first reagent is a hybridization probe. In certain preferred embodiments of this aspect of the invention, the effector is an inhibitor of $PLA_2$, among which uteroglobin is particularly preferred.

Another preferred embodiment of the present invention is directed to a method for preventing or inhibiting metastasis of a cancer of epithelial cell origin, comprising the step of administering to an organism suffering from a cancer of epithelial cell origin a compound that inhibits arachidonic acid release by cells of the cancer by a route and in an amount effective to inhibit or prevent metastasis of the tumor.

In a preferred embodiment of an aspect of the invention in this regard, the compound is an inhibitor of phospholipase $A_2$ or cyclooxygenase. Particularly, phospholipase $A_2$ inhibitors are preferred.

In certain particularly preferred embodiments of this aspect of the invention, the compound is a uteroglobin, a mutein of a uteroglobin, a peptide analog of a uteroglobin, a mimetic of uteroglobin, a lipocortin, a mutein of a lipocortin, a peptide analog of a lipocortin or a mimetic of lipocortin. Especially highly preferred in this regard are methods wherein the compound is a uteroglobin, a mutein of a uteroglobin, a peptide analog of a uteroglobin or a mimetic of uteroglobin. Uteroglobin is preferred and human uteroglobin is particularly highly preferred in this regard.

Also there is provided in accordance with this aspect of the invention certain preferred embodiments in which the compound is a small molecule drug that is a nonsteroidal anti-inflammatory agent. Among these agents inhibitors of phospholipase $A_2$ and cyclooxygenase are preferred. Particularly preferred are mepacrine and indomethacin.

In another regard, preferred embodiments of the present method are those used to treat a cancer of the prostate gland in a human patient.

In further preferred embodiments, the method is used in conjunction with another treatment. In this regard, preferred treatments include surgical intervention, radiation therapy, hormonal therapy, immunotherapy, chemotherapy, cryotherapy or gene therapy.

In accordance with another aspect of the present invention, there has been provided a pharmaceutical composition for inhibiting or preventing metastasis of a cancer of epithelial cell origin, comprising: (i) a compound that inhibits arachidonic acid release by cells of a tumor of epithelial cell origin effective to inhibit or prevent metastasis of the tumor in an organism and (ii) a carrier for effective the therapeutic administration of the compound to the organism.

In certain preferred embodiments of the invention the compound is an inhibitor of phospholipase $A_2$ or cyclooxygenase. In this regard, inhibitors of phospholipase $A_2$ are preferred. In certain particularly preferred embodiments the compound is a uteroglobin, a mutein of a uteroglobin, a peptide analog of a uteroglobin, a mimetic of uteroglobin, a lipocortin, a mutein of a lipocortin a peptide analog of a lipocortin or a mimetic of lipocortin. In especially preferred embodiments in this regard the compound is a uteroglobin, a mutein of a uteroglobin or a peptide analog of a uteroglobin. Among these, uteroglobins are very highly preferred, and human uteroglobins are among the most highly preferred compounds of the present invention.

Also there is provided in accordance with this aspect of the invention certain preferred embodiments in which the compound is a small molecule drug that is a nonsteroidal anti-inflammatory agent. Among these agents inhibitors of phospholipase $A_2$ and cyclooxygenase are preferred. Particularly preferred are mepacrine and indomethacin.

In accordance with another aspect of the invention there has been provided a method for determining metastatic potential of a tumors, particularly those of epithelial cell origin. In certain preferred embodiments of this aspect of the invention there has been provided a method for determining the metastatic potential of tumors of epithelial cell origin comprising the steps of (A) determining an effector of arachidonic acid release in cells in a biopsy sample of a tumor; (B) comparing effector in tumor cells in the biopsy sample with effector in fiduciary cells, and (C) determining metastatic potential, wherein effector in the tumor cells characteristic of normal fiduciary cells or characteristic of fiduciary cells of benign tumors indicates low metastatic potential and effector in the tumor cells characteristic of fiduciary cells of metastatic tumors indicates high metastatic potential.

In some preferred embodiments of this aspect of the invention the effector is an inhibitor of $PLA_2$. In particularly preferred embodiments in this regard, the effector is uteroglobin.

In certain preferred embodiments the effector is determined by assaying the effector protein in cells of the tumor. In particularly preferred embodiments in this regard, the effector is an inhibitor of $PLA_2$. Especially preferred is uteroglobin. In particularly preferred embodiments in this regard the tumor is a prostatic tumor and the inhibitor is uteroglobin.

In another aspect of the invention, preferred embodiments of the invention provide methods for determining metastatic potential in which a protein is assayed by immunocytochemistry. In certain preferred embodiments of this type, the effector is an inhibitor of $PLA_2$. Particularly preferred in embodiments of the invention in this regard is uteroglobin. In particularly preferred embodiments in this regard the tumor is a prostatic tumor and the inhibitor is uteroglobin.

In certain additional preferred embodiments of the invention in this regard, the effector is determined by assaying an mRNA in cells of a tumor. In particularly preferred embodiments in this regard, the mRNA encodes an inhibitor of $PLA_2$. Especially preferred is uteroglobin. In particularly preferred embodiments in this regard the tumor is a prostatic tumor and the inhibitor is uteroglobin.

In certain preferred embodiments in this regard, the mRNA is determined by a method comprising a step of hybridizing a probe to cells fixed on a surface. In certain preferred embodiments of this aspect of the invention the mRNA is determined by in situ hybridization.

In preferred embodiments of the invention in both regards the effector is an inhibitor of $PLA_2$, most particularly uteroglobin. In particularly preferred embodiments in this regard the tumor is a prostatic tumor and the inhibitor is uteroglobin.

In another aspect of the invention in this regard, aberrant mRNA is determined. In preferred embodiments of the invention in this regard, the mRNA encodes an inhibitor of $PLA_2$, most particularly uteroglobin. In particularly preferred embodiments in this regard the tumor is a prostatic tumor and the inhibitor is uteroglobin.

In a still further object of the invention there has been provided a kit for determining metastatic potential of a tumor. In certain preferred embodiments kits of the invention comprise: (A) a first reagent that binds specifically to an effector of arachidonic acid release in cells in a biopsy sample prepared for determination of the effector, and (B) a second reagent for detectably labelling the primary binding reagent bound specifically to cells in the biopsy sample, wherein the determination of the effector tumor is diagnostic of the metastatic potential of the tumor.

In certain preferred embodiments of the kits of the invention, the effector is an inhibitor of $PLA_2$, among which uteroglobin is particularly preferred.

In certain further preferred embodiments of the this aspect of the invention, the first reagent is an antibody. In particularly preferred embodiments in this respect, the effector is an inhibitor of $PLA_2$, among which uteroglobin is particularly preferred.

Additional preferred embodiments of this aspect of the invention are those in which the first reagent is a hybridization probe. In certain preferred embodiments of this aspect of the invention, the effector is an inhibitor of $PLA_2$, among which uteroglobin is particularly preferred. Other objects, features and advantages of the invention will be apparent from the following detailed description. It should be understood, however, that the detailed description and the specific examples, while providing general and specific descriptions and indicating preferred embodiments of the invention, are given by way of illustration only. Various changes and modifications within the spirit and scope of the invention will become apparent to those skilled in the art from the detailed description and other aspects of the present disclosure.

BRIEF DESCRIPTION OF THE FIGURES

FIG. 5 is a graph showing that uteroglobin inhibits arachidonic acid release from FCM-stimulated DU-145 cells over a five hour period. Cells were incubated for 24 hr. in αMEM/SF media containing $^{14}$C-labelled arachidonic acid. Free label then was washed away, and the cells were incubated in FCM without and with 1 $\mu$M uteroglobin. Arachidonic acid release was measured by $^{14}$C released from the cells into the medium.

GLOSSARY

Figure 1:
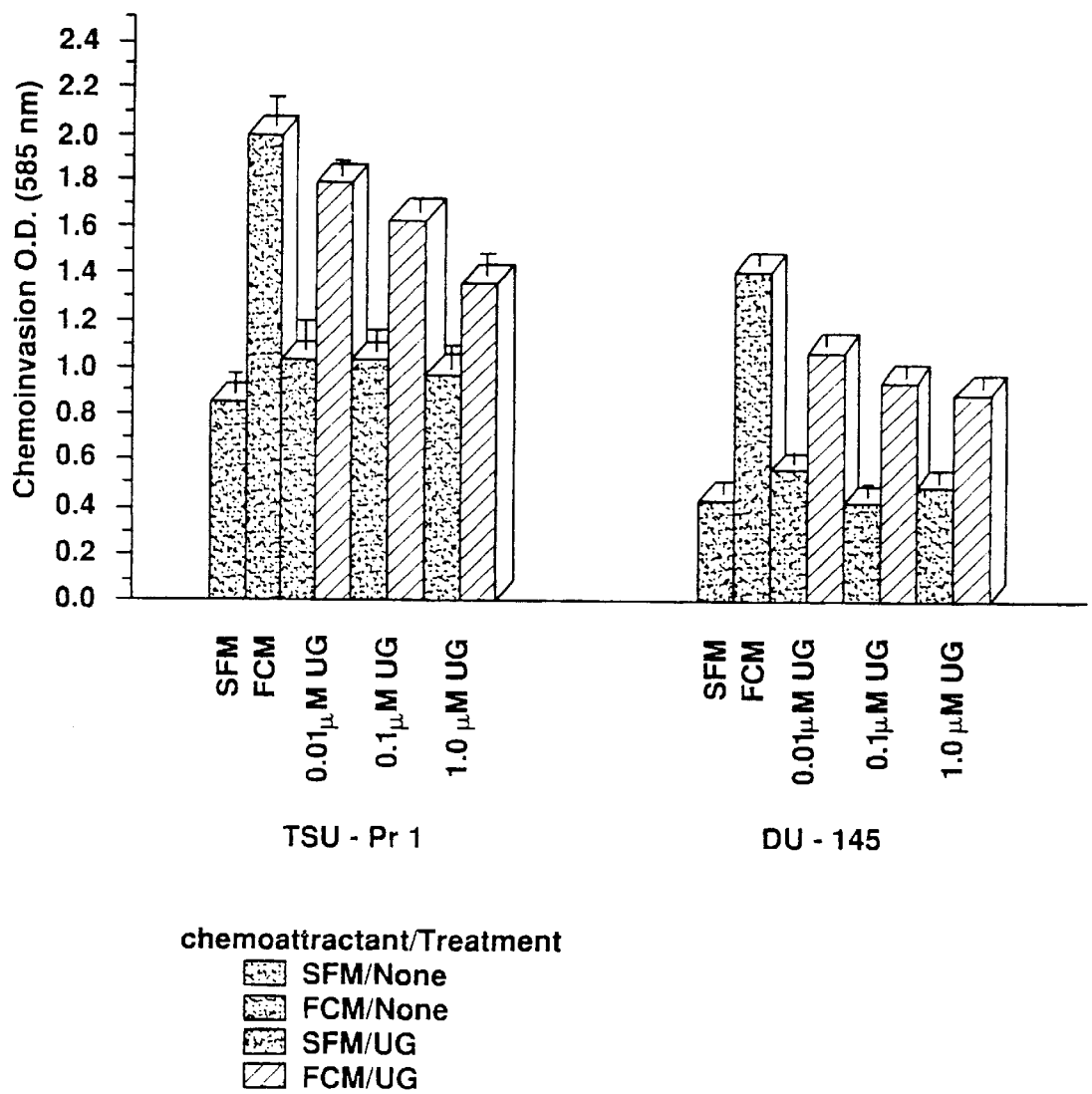
FIG. 1 is a bar chart showing the dose effect of uteroglobin on the invasiveness of cells of the TSU-Prl and DU-145 cell lines, epithelial cell lines derived from human prostate tumors. Both TSU-Prl and DU-145 cells are androgen independent. Cells were cultured in zero, 0.01, 0.1 and 1.0 $\mu$M uteroglobin for 24 hr. Invasiveness then was assayed by migration through filters coated with reconstituted basement membrane (RBM) in response to serum free or fibroblast conditioned media (FCM). Invading cells were stained with crystal violet, the dye was extracted and invasiveness was determined by measuring dye concentration by optical absorbance at 585 nm. Each point in the graph is the mean of results of three separate experiments, each carried out using triplicate cultures. The bars show the standard error of the mean for each point.

The abbreviations and terms in the present disclosure are employed in contemplation of their fullest meaning consistent with the disclosed and claimed invention. The following brief explanations are entirely illustrative and neither exhaustively define nor limit the invention disclosed and claimed herein. The full meaning of the terms will be clear from an understanding of the invention based on contemplation of the disclosure as a whole in light of a full understanding of the pertinent arts.

ARACHIDONIC ACID CASCADE: a series of enzymatic reactions that results in the production and release of arachidonic acid by a cell. The cascade is sensitive to ligand signals and arachidonic acid itself is an autocrine factor.

DU-145: an epithelial cell line derived from a human prostate tumor, which is androgen independent.

LNCaP: an epithelial cell line derived from a human prostate tumor, which is androgen sensitive. The LNCaP cell line was derived from a supraclavicular lymph node metastasis of a human prostate carcinoma. Cells of this line exhibit increased proliferation in response to androgen, in vitro, and they secrete prostate specific antigen (PSA), a marker of differentiated epithelial cells.

TSU-Prl: an epithelial cell line derived from a human prostate tumor, which is androgen independent.

PC3-M: an epithelial cell line derived from a human prostate tumor, which is androgen independent.

EFFECTOR: a substance that engenders, alters, modulates or controls an activity of a cell; a substance that can engender, alter, modulate or control a physiological activity of a cell or organism. Typically, a protein, such as an enzyme, cofactor or transcription regulatory protein, or an activator or inhibitor of an enzyme, an enzyme complex, a receptor or a receptor complex, for instance.

EPITHELIAL CELL ORIGIN: derived from an epithelial cell, of whatever tissue.

FCM: fibroblast conditioned media

FIDUCIARY: a reference against which a test outcome is compared to gauge results. A fiduciary series is a plurality of such references that represent points along a qualitative or a quantitative scale.

IDENTIFYING: in the context of identifying PIN, ascertaining, establishing or otherwise determining one or more factual characteristics of prostatic intraepithelial neoplasia or a similar intermediate condition.

INHIBITION: inhibition of metastasis may be measured by many parameters in accordance with the present invention and, for instance, may be assessed by delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition, is referred to herein as prevention.

METASTASIS: As set out in Hill, R. P., Chapter 11, *Metastasis,* pp178–195 in *The Basic Science of Oncology,* Tannock et al., Eds., McGraw-Hill, New York (1992), which is incorporated by reference herein in its entirety, metastasis is "The ability of cells of a cancer to disseminate and form new foci of growth at noncontiguous sites (i.e., to form metastases)."

Similarly, metastasis is described in Aznavoorian et al., *Cancer* 71: 1368–1383 (1993), which is incorporated by reference herein in its entirety, as "The transition from in situ tumor growth to metastatic disease is defined by the ability of tumor cells of the primary site to invade local tissues and to cross tissue barriers. . . . To initiate the metastatic process, carcinoma cells must first penetrate the epithelial basement membrane and then invade the interstitial stroma. . . . For distant metastases, intravasation requires tumor cell invasion of the subendothelial basement membrane that must also be negotiated during tumor cell extravasation . . . The development of malignancy is also associated with tumor-induced angiogenesis [which] not only allows for expansion of the primary tumor, but also permits easy access to the vascular compartment due to defects in the basement membranes of newly formed vessels."

MIMETIC: a molecule which, in shape and effect, mimics the shape and therefore the activity of another molecule or complex of molecules upon which it is designed.

MUTEIN: An amino acid sequence variant of a protein. The variation in primary structure may include deletions, additions and substitutions. The substitutions may be conservative or non-conservative. The differences between the natural protein and the mutein generally conserve desired properties, mitigate or eliminate undesired properties and add desired or new properties. In the present invention the muteins generally are those that maintain or increase antimetastatic activity. Particularly, uteroglobin muteins are amino acid sequence variants of uteroglobin that maintain or increase the anti-metastatic activity of uteroglobin.

NSAID: Nonsteroidal anti-inflammatory agents. Small molecule drugs, as the term is used herein, that inhibit cyclooxygenase, but do not directly inhibit phospholipase $A_2$. These compounds have been used for their anti-inflammatory action. Aspirin, phenylbutazone, ibuprofen, sulfinpyrazone (Anturane) and indomethacin are NSAIDs.

PEPTIDE ANALOG: an oligo or polypeptide having an amino acid sequence of or related to a protein. Peptide analogs of the present invention are peptides that have anti-metastatic activity and an amino acid sequence the same as or similar to a region of an anti-metastatic protein, such as uteroglobin.

PIN: prostatic intraepithelial neoplasia. A condition associated with prostate cancer having two grades, high grade PIN which may indicate a high risk of prostate cancer, and low grade PIN which may indicate a low risk of prostate cancer. PIN is also known as dysplasia, intraductal dysplasia, large acinar atypical hyperplasia, atypical primary hyperplasia, hyperplasia with malignant change, marked atypia, and duct-acinar dysplasia. Pin may be characterized by a high nuclear/cytoplasmic ratio, hyperchromasia, coarsely granular chromatin, absence of nucleoli, isolated cells and cellular and nuclear pleomorphism.

PLA: phospholipase A $PLA_2$: phospholipase $A_2$

PREVENTION: in relation to metastasis, virtually complete inhibition, no metastasis if it had not occurred, no further metastasis if there had already been metastasis of a cancer. See INHIBITION.

PSA: Prostate specific antigen

RBM: reconstituted basement membrane. A multicomponent matrix approximating the molecular composition of the intracellular tissue matrix and the epithelial cell basement membrane. Preparations for preparing RBM are well known and are available from commercial suppliers.

SFM: Serum free medium

UG: uteroglobin hUG: human uteroglobin

DETAILED DESCRIPTION OF THE INVENTION

Notwithstanding past failures to develop methods to identify prostatic intraepithelial neoplasia or to distinguish nonmetastatic aberrations and tumors with low metastatic potential from aberrations and tumors with high metastatic potential, the present invention provides methods for determining the metastatic potential of aberrant growths, tumors and cancers and for identifying prostatic intraepithelial neoplasia.

In addition, notwithstanding past failures to develop effective anti-metastatic treatments, the present invention provides compounds and compositions for inhibiting cancer metastases and methods for administering the compounds and compositions to inhibit or prevent metastasis of a tumor of epithelial cell origin in an organism.

DETERMINING THE METASTATIC POTENTIAL OF TUMORS

Determining the activity of factors that effect arachidonic acid release in cells can serve to indicate metastatic potential of a tumor. In this regard, determining $PLA_2$ activity, and the activity or abundance of factors that affect the activity of $PLA_2$ can serve to indicate metastatic potential. Determining metastatic potential in accordance with this aspect of the present invention is illustrated by the following discussion of uteroglobin protein, mRNA or DNA as an index of metastatic potential of prostatic tumors, a very particularly preferred embodiment of the invention, which should not be construed as being limitative.

METHODS

Uteroglobin to index metastatic potential

The prostate is the sex gland in males that makes seminal fluid. It is located, in the standing male, vertically below the bladder, where it surrounds the urethra. Generally, it is shaped roughly like a slightly elongated sphere, like a walnut. In most men, it is about an inch in diameter until about age 50 and thereafter it tends to grow larger.

Pathology of the prostate can present as infection, benign enlargement or cancer. Benign growth adversely affects health only when the enlarged prostate constricts the urethra and interferes with urination. Malignant growth always poses a threat to health and life of the patient; although, as discussed below, prognoses and indicated treatments vary greatly between occurrences.

Prostate cancer is the most frequently diagnosed cancer in men in the United States. Prostate cancers generally do not grow quickly. Usually, they double in size only every three or four years. Adverse affects of prostate cancer also develop slowly, as they are effected by the growth of the tumor itself.

The slow progression of prostate cancer presents something of a conundrum in men 50 or older, who present the majority of prostate cancer cases. Often the normal progression of prostate cancer suggests that debilitating effects will not develop within the normal life expectancy of the patient. Given the lack of effective treatments and the deleterious side effects attendant to the treatments currently available, waiting may be the best therapy for many elderly patients.

Unfortunately, it is difficult to distinguish benign from cancerous tumors and, more importantly, slow growing localized tumors from those formed by more aggressive, metastatic cancers. Thus, even the best physician cannot accurately predict the course of progression of a given prostate cancer, and cannot prescribe the best treatment regimen.

In one aspect the present invention overcomes this obstacle to effective treatment of such tumors by providing a method to determine the metastatic potential of prostatic tumors. In accordance with this aspect of the invention, uteroglobin protein, mRNA or DNA is determined in cells of biopsy material. The protein, mRNA or DNA determined in the cells, by comparison to uteroglobin determined in normal cells, indicates the metastatic potential of prostatic tumors, particularly those of epithelial cell origin.

It is worth noting in this respect that previous studies did not identify the relationship between metastatic potential of a tumor and decreased expression of uteroglobin (or any other inhibitors of arachidonic acid release). In previous studies, for instance, uteroglobin (called Clara cell 10 kDa protein, abbreviated CC10) was used as a marker for certain types of cells, and cell-type specificity of its expression was studied. (As described in Linnoila et al., A.J.C.P. 97(2): 235–243 (1992) and Peri et al., J. Clin. Invest. 92: 2099–2109 (1993), which are incorporated by reference herein in their entirety). In addition, CC10 expression was reported to vary between patients and cell types. In particular, it was reported that CC10 expression was lower in lung cancer patients and in smokers without lung cancer than it was in non-smokers, and decreased CC10 expression has been loosely associated with neoplasm. (Broers et al., Lab. Invest. 66: 337–346 (1992) and Jensen et al., Int. J. Cancer 58: 629–637 (1994), which are incorporated by reference herein in their entirety. However, no studies of CC10 expression have suggested that uteroglobin expression in cells of a tumor can be used to determine metastatic potential.

Specific detection of proteins

Proteins indicative of metastatic potential of tumors can be determined in cells in biopsy material by conventional methods well known to those of skill in the art. Such methods are described in many standard textbooks and laboratory manuals. For instance, the techniques for making and using antibody and other immunological reagents and for detecting particular proteins in samples using such reagents are described in CURRENT PROTOCOLS IN IMMUNOLOGY, Coligan et al., Eds., John Wiley & Sons, New York (1995), which is incorporated by reference herein in parts pertinent to making and using reagents useful for determining specific proteins in samples. As another example, immunohistochemical methods for determining proteins in cells in tissues are described in Volume 2, Chapter 14 of CURRENT PROTOCOLS IN MOLECULAR BIOLOGY, Ausubel et al., Eds., John Wiley & Sons, Inc. (1994), which is incorporated by reference herein in part pertinent to carrying out such determinations. Finally, Linnoila et al., A.J.C.P. 97(2): 235–243 (1992) and Peri et al., J. Clin. Invest. 92: 2099–2109 (1993), incorporated herein as referred to above, describe techniques that may used, in part, in this aspect of the present invention.

For instance, uteroglobin can be determined in sample in accordance with the invention by histochemical methods set out in Miyamoto et al., J. Urology 149: 1015–1019 (1993), which is incorporated by reference herein in its entirety. As described therein, for instance, suitable biopsy material is obtained from a patient suspected of having benign prostatic hyperplasia or prostatic carcinoma and immediately placed into 0.01M phosphate buffered saline. Thereafter, the material is immediately processed. It is mounted on a brass plate using rat liver homogenate as an adhesive. The material then is frozen in liquid nitrogen-cooled isopentane. Sections suitable for assay of uteroglobin in cells of the material are sectioned in a cryostat. Sections are obtained across the biopsy material, avoiding parts of the biopsy material that are damaged or deleteriously altered by the removal process.

Sections are dried at room temperature, fixed and then washed. Paraformaldehyde is a particularly useful fixative in this regard, but many other fixatives also can be used. The sections may be pretreated with hydrogen peroxide and a non-ionic detergent, such as Triton X-100. Also, sections may be incubated with a blocking solution to reduce non-specific binding. For instance, the sections may be incubated with goat blocking serum prior to incubation with a goat serum, goat antibody or goat antibody-derived reagent.

Uteroglobin then is visualized for determination in the samples using a uteroglobin-specific binding reagent, such as a monoclonal or a polyclonal anti-uteroglobin antibody. Binding of the uteroglobin-specific reagent to cells in the sections may be determined directly, if the reagent has been conjugated to a detectable label, or using a second or additional reagents, such as a secondary antibody-enzyme conjugate.

In preferred embodiments of the invention, the uteroglobin-specific reagent is an antiserum, a polyclonal antibody, a derivative of a polyclonal antibody, a monoclonal antibody, a derivative of a monoclonal antibody or an engineered antibody, such as a single chain antibody. Derivatives of monoclonal and polyclonal antibodies include conjugates and fragments. Antibodies conjugated to detectable labels are preferred in this regard. Among detectable labels are enzymes such as horseradish peroxidase. Among fragments preferred in this regard are Fab fragments, F(ab')$_2$ fragments and F(ab') fragments.

Sections are incubated with uteroglobin-specific reagent under conditions effective for the uteroglobin-specific reagent to bind efficiently to uteroglobin in said cells, while binding to other cellular components is inefficient; i.e., under conditions effective for the ratio of specific to non-specific binding to provide accurate determination of uteroglobin content in cells of the biopsy material.

At the same time, control sections may be incubated under the same conditions with a corresponding reagent that is not specific for uteroglobin, to estimate background binding. For polyclonal immune serum, for instance, control sections can be incubated with preimmune serum to monitor background, non-specific binding. After the incubation period, the specific reagent, and any reagent used in the controls, is removed, as by washing.

If the primary, uteroglobin-specific reagent is detectably labelled, then the label may be determined and, thereby the uteroglobin content of cells in the sample. In this case, controls preferably would be labeled and would be determined in like fashion. More often, and preferably, a secondary reagent is used to visualize binding of reagents on the sections, as described below.

After removing unbound specific and non-specific reagents, test and control sections are incubated with a secondary reagent that binds specifically to the primary, uteroglobin specific reagent and its counterpart in the controls. Preferably, the secondary reagent is a biotinylated anti-antibody.

The sections are incubated with the secondary reagent under conditions for the reagent to bind efficiently to the primary reagent (and its counterpart in the controls) in the cells, while binding to other cellular components is inefficient; i.e., under conditions effective for the ratio of specific to non-specific binding to provide accurate determination of uteroglobin content in cells of the biopsy material.

Thereafter, the unbound fraction of the secondary reagent is removed from the sections. The secondary reagent, and its counterpart in the controls, then is determined. If the secondary reagent comprises a detectable label, incubation with a tertiary reagent generally will not be necessary. However, use of a tertiary reagent comprising a detectable label is more commonly employed for immunocytochemical analysis, generally. Therefore, for illustrative purposes, the three component assay is described here.

The sections then are incubated with a tertiary reagent comprising a detectable label that binds specifically to the secondary reagent. Incubation is carried out under conditions effective for the tertiary reagent to bind efficiently to the secondary reagent bound to primary reagent in cells in the test sections or its counterpart in control sections, while binding to other cellular components is inefficient; i.e., under conditions effective for the ratio of specific to non-specific binding to provide accurate determination of uteroglobin content in cells of the biopsy material. A preferred tertiary reagent comprising a detectable label is an avidinated enzyme for binding to biotinylated secondary reagent. A preferred enzyme in this regard is horseradish peroxidase.

Unbound tertiary reagent is removed, by washing the sections with buffer, for instance. The detectable label bound in cells in the biopsy material then may be determined. In preferred embodiments of the invention, sections are incubated under conditions effective for an enzyme in the tertiary reagent to catalyze a chromogenic reaction. Binding of the uteroglobin-specific reagent is determined by the color generated by the reaction.

Suitable reagents and conditions for carrying out the determination of uteroglobin in cells in biopsy samples are well known and readily available. A multiplicity of procedures and reagents can be effectively employed for this purpose. Such reagents and techniques routinely are employed by those of skill in the arts of immunocytochemistry, histopathology and cytology.

Kits for performing such assays, in whole and in part, are widely available from numerous commercial suppliers. Incubation with secondary antibodies, and subsequent visualization of uteroglobin, can carried out according the given procedures prescribed by commercial suppliers.

In preferred embodiments the sections are stained with hematoxylin and eosin to confirm pathology and to facilitate comparison of uteroglobin in normal and diseased cells in the same section.

In particularly, preferred embodiments, the relative staining of diseased and normal cells in a sections is compared with staining in fiduciary cells. The fiduciary cells are reference standards which typify results obtained by a given procedure in normal cells, cells characteristic of benign tumors, and cells characteristic of malignant tumors. Within any category, moreover, fiduciary cells may provide a graded series of characteristic results. Uteroglobin in fiduciary cells may be determined at the same time uteroglobin is determined in cells of the biopsy sample, or at another time. In a particularly preferred embodiment of the invention, uteroglobin is determined in fiduciary cells which serve as a standard reference series for subsequent clinical assays.

In normal tissue immunocytochemical techniques, such as those described above, reveal very heavy staining of uteroglobin in the luminal surface of prostatic epithelial cells. Biopsy samples that evidence intermediary pathology thought to precede neoplasia, such as prostatic intraepithelial neoplasia ("PIN"), show a pattern of uteroglobin staining similar but weaker than that of normal cells. Biopsy material from malignant tumors shows significant decreases in staining of uteroglobin in cells. The decrease in staining of the luminal surface of epithelial cells in prostatic tumors is particularly dramatic. Whereas, in normal tissue the luminal surface of epithelial cells shows the highest staining for uteroglobin, uteroglobin staining either cannot be detected or is faint in the same cells in metastatic prostatic tissue.

It is this ability to differentiate between normal tissue, prostatic intraepithelial neoplasia, and cancer which provides for the identification of PIN. Due to the association of PIN with cancer, especially high-grade PIN which has been reported to have a 70% association with cancer, this provides an early diagnosis, prognosis and treatment of prostate cancer.

Furthermore, it has been reported that there is a close relationship between the age-related prevalence of PIN and the age-related prevalence of prostate cancer with the occurrence of PIN mirroring the occurrence of prostate cancer but having a 20–30 year lag time. It is this relationship which provides a practitioner the diagnostic and prognostic ability of early detection and treatment.

The risk of developing invasive cancer is gauged by the decrease in uteroglobin in diseased cells in the biopsy sample relative to cells in normal tissue of the same type, as described above. In biopsy material containing both normal and diseased tissue the staining of cells in the normal and diseased tissue can be compared on the same section. In general, the cells in low grade relatively confined tumors express uteroglobin in amounts similar to normal cells. The cells in aggressive, invasive tumors express little or no uteroglobin and are poorly differentiated in their morphology.

Specific detection of mRNA and DNA mRNA also can be determined in cells in biopsy samples to determine metastatic potential. mRNA can be determined by a variety of methods well known to those of skill in the art, which can be carried out using well known and readily available starting materials, including those widely available from commercial suppliers. Techniques useful in this regard are described in the foregoing references. Techniques that may be particularly pertinent in this regard relating to uteroglobin are described in Broers et al., *Lab. Invest. 66: 337–346* (1992) and Jensen et al., *Int. J. Cancer* 58: 629–637 (1994), incorporated herein as referred to above.

A given mRNA may determined in cells of biopsy tissue by in situ hybridization to a specific probe. Such probes may be cloned DNAs or fragments thereof, RNA, typically made by in vitro transcription, or oligonucleotide probes, usually made by solid phase synthesis. Methods for making and using probe suitable for specific hybridization in situ are ubiquitously known and used in the art.

By specific hybridization is meant that the probe forms a duplex with the given, target mRNA that is stable to the conditions of hybridization and subsequent incubations and that duplexes formed between the probe and other, non-target mRNAs are not stable and generally do not persist through subsequent incubations. Specific hybridization thus means that the ratio of hybridization to target and non-target mRNAs provides an accurate determination of the target mRNA in cells in the biopsy sample.

In a particularly preferred embodiment of the present invention a probe that hybridizes specifically to uteroglobin mRNA is used to determine uteroglobin mRNA in cells of biopsy tissue, particularly prostatic biopsy material.

Techniques suitable for in situ determination of target mRNAs, such as uteroglobin mRNA, are described in a variety of well known and readily available laboratory manuals, as well as the primary literature. An illustrative procedure from the primary literature in this regard is described in Broers et al. *Laboratory Investigation* 66 (3): 337–346 (1992), which is incorporated by reference herein in its entirety.

In general, biopsy material is obtained by suitable surgical procedure and snap frozen, as by freezing in methybutane/dry ice. The samples can be embedded and sectioned much as described above for the determination of protein is biopsy samples. Sections can be thawed onto and affixed to glass slides previously cleaned with acid and ethanol and coated with poly-L-lysine. The tissue sections thereafter can be exposed to buffered formaldehyde, acetylated, treated with buffered glycine and then prehybridized in 50% formamide, 2X SSC (where 1X SSC is 0.15M NaCl, 0.015M sodium citrate, pH 7.0). After prehybridization the sections can be hybridized to the labelled probe in 50% formamide, 10% dextran sulfate, 2X SSC.

The exact conditions of the steps in the procedure, especially the prehybridization, hybridization and criterion steps will be adjusted with the $T_m$ (or the $T_d$) of the probe and to provide the desired degree of specificity of hybridization; i.e., the desired stringency.

Theoretical approximations and empirical methods for determining proper conditions in this regard are well known and routinely practiced by those skilled in the pertinent arts. Approximation calculations and experimental techniques in this regard are described, for instance, in Sambrook et al. (1989) referred to herein above.

Those of skill will appreciate, for instance, that the formamide in the foregoing solutions serves to provide equivalent hybridization conditions at lower temperature. For instance, hybridization in 50% formamide at about 50° C. provides conditions similar to hybridization at 65° C. without formamide. The lower temperature of hybridization can help preserve the biopsy sections during the hybridization procedure, aiding subsequent identification and examination of cells and mRNA content. Other agents that preserve features of the tissue sections that aid analysis likewise are preferred.

Dextran sulfate generally is used to accelerate the hybridization reaction and to drive it to completion in a shorter period of time, as is well known. Similar agents that increase the rate of hybridization, consistent with accurate determination of specific mRNA content, also are useful in the present invention.

Following hybridization, the probe-containing solution and unbound probe are removed. Typically, the sections are washed several times with prehybridization buffer, such as 50% formamide, 2X SSC, at or slightly above the hybridization temperature.

If an RNA probe is used for detection of the target mRNA, the sections then are treated with RNAseA, typically in the same solution, and then washed to remove RNAseA and byproducts with 50% formamide, 2X SSC under the same conditions as the previous washings.

Finally, the sections typically are washed several additional times in 2X SSC at room temperature and then air dried.

Radioactive probes generally are visualized by autoradiography. For this purpose slides can be dipped in a photographic emulsion, dried and allowed to expose the emulsion at 4° C. for an appropriate period of time. Using a preferred emulsion, NTB-2 nuclear track emulsion, exposure times of 3 to 7 days are appropriate. The exposure time can be altered by a variety of factors including the use of more highly labelled probes.

The emulsions are developed at the end of the exposure period and then, typically, counterstained with hematoxylin and eosin. Subsequently, labelling of target mRNA in cells can be assessed by microscopy using brightfield and darkfield illumination.

As discussed above regarding protein, the abundance and distribution of the target mRNA in cells in the biopsy section indicates the metastatic potential of the tumor. Particularly, the relative abundance of mRNA in diseased and normal cells indicates metastatic potential.

A variety of controls may be usefully employed to improve accuracy in assays of this type. For instance, sections may be hybridized to an irrelevant probe and sections may be treated with RNAseA prior to hybridization, to assess spurious hybridization.

Thus, for instance, as discussed for uteroglobin protein, normal tissue exhibits high concentrations of uteroglobin mRNA in the prostatic epithelial cells. Intermediary pathology, such as prostatic intraepithelial neoplasia ("PIN"), shows a lower concentration of uteroglobin mRNA similar to but less than the hybridization to a uteroglobin mRNA-specific probe exhibited by normal cells. Biopsy material from malignant tumors shows significant decreases in the concentration of mRNA uteroglobin in cells by exhibiting little or no hybridization to a uteroglobin mRNA-specific hybridization probe.

Again, the differentiation between normal tissue, prostatic intraepithelial neoplasia, and cancer provides for the identification of PIN and an early diagnosis, prognosis and treatment of prostate cancer.

aberrant mRNA or DNA

Some metastatic tissues of prostatic origin exhibit seemingly normal hybridization to a uteroglobin-specific probe, even though cells in the same tissue do not synthesize much, if any, uteroglobin protein. These cells typically exhibit aberrant uteroglobin mRNA, rather decreased uteroglobin mRNA. For instance, aberrant splicing has been demonstrated in at least one human prostatic carcinoma.

Splicing and other aberrations in mRNAs of cells of metastatic tissue can be determined by northern and southern blotting techniques and by PCR techniques. These techniques also are well known to those of skill in the art and can be applied readily to the determination of mRNA in cells of biopsy material in accordance with the present invention.

Techniques employed to assess restriction fragment length polymorphisms ("RFLP") can be applied to detect some mutations associated with aberrant splicing patterns. The assessment always can be made on the mRNA, but in some dysfunctions it can be made on the genomic DNA as well. The mRNA or DNA can be amplified prior to RFLP analysis, as well, using PCR or other suitable technique.

In addition to RFLP techniques, SSCP can be used to detect aberrant splicing of messages, such as uteroglobin-specific mRNA. For this purpose, a target mRNA, such as uteroglobin mRNA, is amplified by reverse transcriptase-mediated PCR. The double-stranded amplified DNA is denatured and run on gels in which mobility is quite sensitive to small changes in secondary structure.

Yet another technique that can be employed to determine aberrant splicing, among other things, is ligase mediated PCR. This technique also is well known to those of skill in the art, and techniques suitable to the analysis and determination of mRNAs and genomic aberrations that have been described in the literature readily can be applied to the determination of aberrant mRNAs in cells of tumor.

In regard to all of the foregoing, the determination of mRNA and genomic DNA in epithelial cells in biopsy material is preferred. Particularly preferred in this regard is prostatic biopsy material.

Among probes and hybridization targets for determination of metastatic potential of tumors by determination of target mRNA and DNA are probes specific for uteroglobin mRNA or for aberrations of uteroglobin mRNA or uteroglobin-encoding DNA indicative of altered expression of uteroglobin and, therefore, of metastatic potential.

FIDUCIARIES

Fiduciaries may be developed in accordance with this aspect of the invention, to guide interpretation of results. In this regard, a protein or mRNA in accordance with the foregoing may be determined in biopsy material from representative tumors of a specific type, characteristic of a specific degree of metastatic potential.

Characterization in this regard may benefit from hindsight, following the actual course of tumor progression in patients as they undergo treatment and thereafter. Fiduciary results characterizing a graded series of metastatic potential also may obtained from cell culture studies, as described elsewhere herein, illuminated in the examples below.

The determination of a protein or mRNA, or other agent, as set out above, in a variety of tumors of known metastatic characteristic, and the correlation of the determinations with metastatic potential is another preferred embodiment of the present invention.

KITS

Reagents for carrying out the methods described above may be incorporated into kits for use in determining the metastatic potential of a tumor or identifying prostatic intraepithelial neoplasia. All of the techniques and reagents discussed herein with regard to the determination of metastatic potential and identifying prostatic intraepithelial neoplasia, including reagents and methods set out in the examples below may be included in these kits. Preferred kit components generally are those that detect the agents discussed elsewhere herein, particularly as discussed in the foregoing sections pertaining to determination of a protein or mRNA diagnostic of metastatic potential or PIN.

The kits also may include one or more fiduciary results, such as reference slides of immunocytochemical results characteristic of a tumors with high and low metastatic potential, or reference slides of in situ hybridization results characteristic in the same regard. Preferably in this regard, are kits that include a fiduciary series for interpreting results. The fiduciary may be in the form of one or more photographs or may be depicted in other ways, including written descriptions. In addition, the fiduciary may be highly tumor-type-specific or it may be applicable to related types of tumors.

ANTI-METASTATIC AGENTS AND METHODS

The invention disclosed herein provides agents and methods for inhibiting or preventing metastasis. The following discussion illustrates the invention in this respect.

Anti-metastatic agents

In particular, in accordance with this aspect of the invention, which include compounds that inhibit arachidonic acid release by cells of a tumor of epithelial cell origin in an organism are administered by a route and in an amount effective to prevent or inhibit metastasis of the tumor.

Inhibitors of arachidonic acid release

Without being limited to any theory of the invention, applicants note that arachidonic acid is a substrate in the synthetic pathway of eicosanoids in cells. Various eicosanoids play a role in stimulating or inhibiting shape, attachment, motility and proliferation of cells. In some aspects of the invention, inhibiting arachidonic acid release in cells of tumors of epithelial cell origin inhibits or extinguishes metastatic potential.

Inhibitors of phospholipase $A_2$

Compounds that inhibit phospholipase $A_2$ ($PLA_2$) are preferred compounds of the present invention. $PLA_2$ is a membrane signaling enzyme of the arachidonic acid cascade, the series of enzymes, substrates, products and co-factors involved in the production and secretion of arachidonic acid, and it generally will be the case that inhibitors of $PLA_2$ activity generally will inhibit release of arachidonic acid. Notably, $PLA_2$ has been associated with processes of inflammation, rather than tumorigenesis or metastasis, and it has been suggested as a target for the control of chronic inflammation, but not as a target for developing an anti-metastatic agent. Nevertheless, the present invention provides compositions and methods of $PLA_2$ inhibitors for inhibiting metastasis of tumors of epithelial cell origin. The formulation and use of these compounds in the invention is illustrated by reference to the preferred embodiments discussed below.

Especially preferred among $PLA_2$ inhibitors are lipocortins, muteins of lipocortins, peptide analogs of lipocortins and uteroglobins, muteins of uteroglobins and peptide analogs of uteroglobin. Uteroglobins, muteins of uteroglobins and peptide analogs of uteroglobin are particularly preferred. Most particularly preferred are uteroglobins, and among these human uteroglobin is very especially preferred. The discussion below, directed to uteroglobin, particularly human uteroglobin, illustrates the invention is this regard.

Uteroglobins

Uteroglobin, also called blastokinin, was first discovered as a major protein component of the rabbit uterine fluid during early pregnancy. The human counterpart to rabbit uteroglobin was first found in nonciliated Clara cells in the distal bronchiole airway and was originally designated Clara cell 10 kD protein, abbreviated as "CC10." Uteroglobin also has been detected in humans in the uterus, respiratory tract, and prostate gland, by immunohistochemical methods.

The complementary DNA for human uteroglobin (CC10) has been cloned and its sequence has been determined, as reported in Singh et al., *BBA* 950: 329–337 (1988), incorporated by reference herein in its entirety.

Uteroglobin has been purified to homogeneity by at least two groups and it has been structurally and functionally characterized in considerable detail. In brief, uteroglobin occurs in rabbits as a dimer of two identical chains. The monomers are 70 amino acids long. They are arranged antiparallel to one another in the dimer. Also, in the dimer they are covalently linked by two symmetrical disulfide bonds, formed between 'Cys-3' and "Cys-69" and, reciprocally, between 'Cys-69' and "Cys-3" (where ' designates one chain in the dimer and " designates the other chain). Each monomer chain contains four α-helical segments and a β-turn, the later at Lys-26 to Gln-29. The structure, function and activities of uteroglobin has been reviewed, for instance, by Miele et al., *Endocrine Reviews* 8: 474–490 (1987), which is incorporated by reference herein in its entirety.

Uteroglobin inhibits the activity of $PLA_2$, as shown by in vitro assays. Generally, it has been thought to have immunomodulatory or anti-inflammatory activities, or both, that act to protect the wet epithelia of organs that communicate with the external environment. Uteroglobin expression is steroid-sensitive and its secretion in the endometrium has been shown to be stimulated by progesterone. Uteroglobin also has been reported to have an anti-chemotactic effect on neutrophils and monocytes. Uteroglobin has not been seen as playing a role in cancer or metastasis. Thus, it was surprising to find that uteroglobin, in accordance with the present invention, can be used to inhibit or prevent metastasis of a tumor of epithelial cell origin in an organism.

Without being bound to any theory of the mechanism by which uteroglobin inhibits metastasis, it appears, as the Examples show, that the inhibitory action of uteroglobin on metastasis results from inhibition of $PLA_2$ activity and inhibition of arachidonic acid release by the tumor cells. Any uteroglobin may be useful in the invention that inhibits arachidonic acid release that inhibits or prevents metastasis of a tumor of epithelial cell origin. Uteroglobins for use in the invention may be recovered from natural sources, it may be made by recombinant means, it may be produced by chemical techniques, it may be made by semi-synthetic methods or it may be obtained by a combination of techniques.

Methods for purifying uteroglobin to homogeneity from a natural source have been described in Nieto et al., *Arch. Biochem. Biophys.* 180:80–92 (1977), which is herein incorporated by reference in its entirety. Other methods for this purpose can be equally useful in this regard.

The most highly preferred uteroglobin for use in the invention at the present time is human uteroglobin. Preferably, human uteroglobin for use in the invention is made by expression of a cloned gene in a host cell in culture or in an animal. Techniques for expressing uteroglobin in this way are well known to those of skill in the art.

A cDNA encoding human uteroglobin, useful toward this end, has been isolated, sequenced and expressed in cells in culture. Methods for expressing cloned DNAs that encode uteroglobin have been described specifically with regard to human uteroglobin in Mantile et al., *J. Biol Chem.* 268: 20343–20351 (1993) and Miele et al., *J. Biol. Chem.* 265: 6427–6435 (1990), which, as noted below, are incorporated by reference herein in their entirety.

Techniques for obtaining, manipulating and expressing cloned genes to obtain uteroglobin for use in the present invention are well known to those of skill in the art and are described in protocol-like detail in a variety of laboratory manuals. For instance, such methods are set forth in Sambrook et al., MOLECULAR CLONING: A LABORATORY MANUAL, 2ND Ed., Cold Spring Harbor Laboratory Press, Cold Spring Harbor, N.Y. (1989), the entirety of which is herein incorporated by reference.

Lipocortins

Lipocortin proteins also are known as annexins, and are well known to the art. They generally have been characterized as calcium-dependent phospholipid-binding proteins. For instance, Arcone et al., *Eur. J. Biochem,* 211: 347–355 (1993), incorporated by reference herein in its entirety, reports on the structure of human lipocortin 1 and the expression of the active protein using an expression vector in *E. coli*.

Lipocortins have been implicated in the mechanism of anti-inflammatory activity of glucocorticosteroids. Furthermore, anti-inflammatory activity has been associated with the amino-terminal end of human lipocortin 1, as shown by the activity of acylated polypeptide corresponding to human lipoprotein residues 2–26, synthesized and characterized by Cirino et al., *J. Pharmacol.* 108: 573–4 (1993), which is incorporated by reference herein in its entirety.

According to one hypothesis, lipocortins mediate a glucocorticosteroid-dependent inhibition of phospholipase $A_2$. Some studies support a "substrate-depletion" mechanism of phospholipase $A_2$ inhibition, as reported by Bastian et al., *J. Invest. Dermatol.* 101: 359–63 (1993), for instance, which is incorporated by reference herein in its entirety.

The studies have focused on the intermediary role of lipocortins in the anti-inflammatory response to glucocorticosteroids, however, and a role for the lipocortin proteins in metastasis was unknown.

In accordance with one aspect of the present invention, lipocortins may be used to inhibit or present metastasis of tumors of epithelial cell origin. The methods of using lipocortins, and the compositions of lipocortins, in accordance with the present invention, will be understood by reference to the discussion elsewhere herein, particularly by reference to the illustrative disclosure relating to uteroglobin and to prostate cancers.

Lipocortins generally may be used in accordance with this aspect of the present invention. Preferred lipocortins have a high therapeutic effect and low incidence of deleterious side effects. Particularly preferred lipocortins are those of human origin. Human lipocortin 1 is among those particularly preferred.

Muteins and peptide analogs

Techniques such as those described in the foregoing manual can be used to make variants and analogs of uteroglobin and other proteins useful in the invention. Recombinant DNA methods, chemical synthetic methods, enzymatic methods and mixed methods for making, altering and utilizing muteins and peptide analogs are well known and are described here only briefly to illustrate their applicability to the present invention.

-muteins

It will be appreciated by those of skill that cloned genes readily can be manipulated to alter the amino acid sequence of a protein. The cloned gene for human uteroglobin can be manipulated by a variety of well known techniques for in vitro mutagenesis, among others, to produce variants of the naturally occurring human protein, herein referred to as muteins, that may be used in accordance with the invention.

The variation in primary structure of muteins of lipocortins or uteroglobins useful in the invention, for instance, may include deletions, additions and substitutions. The substitutions may be conservative or non-conservative. The differences between the natural protein and the mutein generally conserve desired properties, mitigate or eliminate undesired properties and add desired or new properties. In the present invention the muteins generally are those that maintain or increase anti-metastatic activity. Particularly, uteroglobin muteins are amino acid sequence variants of uteroglobin that maintain or increase the anti-metastatic activity of uteroglobin.

-peptide analogs

Similarly, techniques for making small oligopeptides and polypeptides that exhibit activity of larger proteins from which they are derived (in primary sequence) are well known and have become routine in the art. Thus, peptide analogs of proteins of the invention, such as peptide analogs of lipocortin and uteroglobin that exhibit anti-metastatic activity also are useful in the invention.

Mimetics

Mimetics also can be used in accordance with the present invention to prevent or inhibit metastasis of tumors. The design of mimetics is known to those skilled in the art, and generally are understood to be peptides or other relatively small molecules that have an activity the same or similar to that of a larger molecule, often a protein, on which they are modeled.

Thus, by way of illustration, uteroglobin mimetics, for instance, can be used in accordance with the present invention in the same manner as uteroglobin itself, to prevent or inhibit metastasis of a tumor.

The design of such mimetics can be based on the structure-function relationship of uteroglobin. By studying the effect of mutations on anti-metastatic activity of uteroglobin the sites in the protein responsible for anti-metastatic activity can be identified. In vitro mutagenesis procedures that can be used to systematically alter cloned genes, such as cDNAs encoding uteroglobin and other proteins with anti-metastatic activity of the present invention, are described in Sambrook et al. (1988). Systematically mutagenized proteins, also referred to as muteins as noted elsewhere herein, can be produced using such altered DNA by standard methods for expression cloned genes in organisms to produce heterologous proteins. Such methods are well known to those of skill and are described in, for instance, Sambrook et al. (1988) referred to herein above. The muteins so produced then can be assayed for anti-metastatic activity, using in vitro or in vivo assays that model or measure metastatic activity. Suitable methods are described herein and illustrated in the examples below.

Methods for determining aspects of protein structure also are well known to those of skill in the art. To some extent, the structure of a given protein can be approximated by analogy to structures of related proteins. Physical and chemical information about a protein structure can be obtained by a wide variety of well known techniques, including active site modification techniques, NMR, and X-ray crystallography.

This information can be combined with information from studies that correlate structural alterations with changes in activity, such as the mutagenesis studies described above, to generate a map of the shape and chemical functions important to a given activity of a protein.

Molecules that mimic the shape and chemical functionality that provide the desired activity, then can be designed and synthesized. Computer modeling methods that can be employed toward this end, as well as methods of organic synthesis, peptide synthesis and for the synthesis of other classes of compounds that can be used to produce mimetics in accordance with this aspect of the invention are well known to those of skill in the art.

Once a mimetic has been designed and synthesized, it can be assayed for anti-metastatic activity using techniques for this purpose, such as those described elsewhere herein.

Results of activity studies and of structural studies of the mimetics themselves can be used to design further mimetics that are more effective, have fewer undesirable side effects, or have additional activities, such as by combining two mimetics in a single molecule.

In the same manner as for uteroglobin, mimetics can be designed for other compounds that have anti-metastatic activity. Preferred in this regard, as described above, as anti-metastatic mimetic compounds that inhibit arachidonic acid release by cells of a cancer of epithelial cell origin. Particularly preferred are mimetics that inhibit phospholipase $A_2$ in such cells. In this regard, mimetics of uteroglobin or lipocortin are especially preferred. Among the most highly preferred mimetics in this regard are mimetics of human uteroglobin.

Small molecule drugs

Compounds other than the proteins, muteins, protein-derived peptides, mimetics and the like discussed above, that inhibit arachidonic acid release by cells of cancers of epithelial cell origin also may be useful in the present invention. Among such compounds are certain small organic molecules, which may be mimetics, that inhibit arachidonic acid release. Inhibition may be mediated by inhibition of $PLA_2$ activity, or by inhibition of other enzymes or intermediates involved in metabolic interactions that result in arachidonic acid release.

Among such compounds is the anti-inflammatory agent mepacrine, which has been shown to inhibit $PLA_2$, and an experimental drug, indomethacin, which has been shown to inhibit cyclooxygenase. Both compounds and exhibit anti-metastatic activity in in vitro assays, at doses that have been shown to be non-toxic in patients. Both compounds, thus, can be utilized in accordance with the present invention.

$PLA_2$, as noted herein above, is a key enzyme in the arachidonic acid cascade. As noted above, inhibitors of $PLA_2$ are most preferred in the invention, in this regard. Among small molecule drugs, mepacrine is preferred among inhibitors of $PLA_2$. Other relatively small molecule drugs (small, in this case, meaning small relative to proteins of average size) that, like mepacrine, inhibit $PLA_2$ also will be useful in the invention, in the same fashion as mepacrine and the other $PLA_2$ inhibitors discussed herein above. Among small molecule drugs, such $PLA_2$ inhibitors are particularly preferred. In this regard, mepacrine is highly preferred and other compounds that are similar to mepacrine in chemical structure are particularly preferred.

Cyclooxygenase is the key enzyme in the cyclooxygenase-dependent pathway of arachidonic acid metabolism, wherein arachidonic acid is a precursor in the synthesis of prostaglandins, prostacyclins and thromboxanes. Among small molecule drugs, inhibitors of cyclooxygenase also are preferred for use in the invention disclosed herein. Nonsteroidal anti-inflammatory agents ("NSAIDs") are among the small molecule drugs, as the term is used herein, that inhibit cyclooxygenase and are preferred in the invention in this regard. NSAIDs are described, for instance, in PRINCIPLES OF PHARMACOLOGY, Munson et al., EDs., Chapman & Hall, New York (1995), which is incorporated herein by reference in part pertinent thereto, including, particularly, Chapter 74.

Among NSAIDs in accordance with this aspect of the invention are aspirin, phenylbutazone, ibuprofen, sulfinpyrazone (Anturane) and indomethacin. In this regard, indomethacin is particularly preferred and compounds that are similar to indomethacin in chemical structure also are preferred.

Lipoxygenase is the key enzyme in the lipoxygenase-dependent pathway of arachidonic acid metabolism, wherein arachidonic acid is a precursor in the synthesis of thromboxanes. Inhibitors of lipoxygenase, and other downstream enzymes of the lipoxygenase-dependent pathway also may be of use in the present invention.

Compositions

Any non-toxic, inert and effective carrier may be used to formulate compositions of the present invention. Well known carriers used to formulate other therapeutic compounds for administration to humans particularly will be useful in the compositions of the present invention. Pharmaceutically acceptable carriers, excipients and diluents in this regard are well known to those of skill, such as those described in the MERCK INDEX, 11th Ed., Budavari et al., Eds., Merck & Co., Inc., Rahway, N.J. (1989), which is incorporated by reference herein in its entirety. Examples of such useful pharmaceutically acceptable excipients, carriers and diluents include distilled water, physiological saline, Ringer's solution, dextrose solution, Hank's solution and DMSO, which are among those preferred for use in the present invention.

In particular, for instance Mantile et al., *J. Biol Chem.* 268: 20343–20351 (1993), incorporated by reference hereinabove, report on sterile formulated, lyophilized uteroglobin that may be useful in preparing uteroglobin compositions of the invention.

Cancers

Methods and compositions of the present invention may be applied to the treatment of a variety of cancers of epithelial cell origin. Among these are metastatic cancers of breast, lung, colon, bladder, prostate, gastrointestinal track, endometrium, tracheal-bronchial tract, pancreas, liver, uterus, nasopharynges and the skin. An especially preferred target is prostate cancer, particularly prostate cancer of epithelial cell origin.

The following detailed discussion of prostate cancers is provided in illustration of the compositions and methods of the invention not only as to prostate cancers, but also other cancers that may be treated in analogous or identical fashion, in accordance with the present invention.

Prostatic adenocarcinoma

Adenocarcinoma of the prostate is one of the most common malignancies. It is estimated that 240,000 new cases of prostate cancer will be diagnosed in the United States in 1995, and that it will cause more than 50,000 deaths during the year. In fact, prostate adenocarcinoma is the second leading cause of cancer-related mortality in the United States.

With prostate cancer, as with all solid tumors, it is the metastatic encroachment of the tumor on other vital function that causes the demise of the patient. Approximately 10% of patients are diagnosed initially with metastatic disease. Ultimately, 30–40% of patients with this cancer will develop metastatic disease. Once metastasis occurs there is a the cancer follows a relentless progression.

Invasion is a prerequisite for migration of tumor cells. In connective tissue, stroma and basement membranes form the major physical barriers to the migration process. Invasion of the local extracellular matrix (ECM) by tumor cells thus can be marked as the first step in metastasis. The sequential biochemical mechanism of ECM invasion first involves cell attachment to specific components of ECM followed by a progressive cascade of proteolytic dissolution. Prostate cancers which grow to a critical size exhibit extracapsular invasion and metastasize to specific anatomical sites apparently in response to stromal cell secretory proteins which are necessary for their growth and proliferation. Invasive migration of tumor cells within the prostate gland may occur as a function of chemokinesis along anatomical paths of least resistance, such as the perineural duct. Further establishment of metastasis relies upon successful penetration of the circulatory or lymphatic system, followed by vessel extravasation at the secondary organ, which frequently is bone tissue for cancers of prostatic origin. Nearly all of these steps, including attachment, matrix degradation and migration, can be modeled experimentally in vitro by measuring invasion of a reconstituted basement membrane (RBM) barrier in response to fibroblast-conditioned medium (FCM) which serves as a chemo-attractant.

In vivo, of growth and proliferation of prostate tumor cells primarily is responsive to stromal cell (fibroblast) secretory proteins. Extracapsular invasiveness of prostate tumor cell can be modeled by migration of tumor cells in vitro into reconstituted basement membrane (RBM) in the presence and absence of a chemoattractant, such as fibroblast conditioned medium (FCM). The assay determines cells that have attached to the RBM, degraded the RBM enzymatically and, finally, cells that have towards the FCM side of the membrane. The events in the in vitro invasion assay comport with the important steps observed in the metastatic spread of tumor cells through the basement membrane in vivo.

Prostate tumors frequently initially metastasize to regional lymph nodes, having disseminated through the lymphatic circulation. They also spread to other sites through the vascular system, which is extensively interconnected to the lymphatics. The final site of formation of metastasis is a function of a number of parameters, including: (i) the first capillary bed encountered by blood vessels draining the tumor, and (ii) organ preference of the tumor cells with respect to characteristics of specific tissues that nurture attachment and growth of tumor cells with metastatic potential.

Metastatic potential of prostate cancers of epithelial cells origin can be inhibited by compositions and methods of the invention. In particular, metastasis of these cancers can be inhibited by human uteroglobin, as shown by the examples set out herein below.

Route of administration

Therapeutic treatment with uteroglobin can utilize any type of administration including topical, other non-invasive and invasive means.

Administration by non-invasive means may be by oral, intranasal or transdermal routes, among others.

Generally, at the present time, invasive techniques are preferred. Administration by invasive techniques may be intravenous, intraperitoneal, intramuscular or directly in tumors, among others.

Administration may be by a single dose, it may be repeated at intervals or it may be continuous. Since uteroglobin is small, easily diffusible, and relatively stable it is well suited to long-term continuous administration, such as by perfusion pump. Where continuous administration is applied, infusion is preferred. In this situation, pump means often will be particularly preferred for administration. Especially, subcutaneous pump means often will be preferred in this regard.

In other situations it will be desirable to administered uteroglobin and other agents of the present invention by intramuscular self-injection on a regular basis.

Compositions and methods of the invention also may utilize controlled release technology. Thus, for example, uteroglobin may be incorporated into a hydrophobic polymer matrix for controlled release over a period of days. Such controlled release films are well known to the art. Examples of polymers commonly employed for this purpose that may be used in the present invention include nondegradable ethylene-vinyl acetate copolymer and degradable lactic acid-glycolic acid copolymers. Certain hydrogels such as poly(hydroxyethylmethacrylate) or poly (vinylalcohol) also may be useful, but for shorter release cycles then the other polymer releases systems, such as those mentioned above.

Dose

The quantity of the active agent for effective therapy will depend upon a variety of factors, including the type of cancer, means of administration, physiological state of the patient, other mendicants administered, and other factors.

Treatment dosages generally may be titrated to optimize safety and efficacy. Typically, dosage-effect relationships from in vitro studies initially will provide useful guidance on the proper doses for patient administration. Studies in animal models also generally may be used for guidance regarding effective dosages for treatment of metastatic cancers in accordance with the present invention.

These considerations, as well as effective formulations and administration procedures are well known in the art and are described in standard textbooks, such as GOODMAN AND GILMAN'S: THE PHARMACOLOGICAL BASES OF THERAPEUTICS, 8th Ed., Gilman et al. Eds. Pergamon Press (1990) and REMINGTON'S PHARMACEUTICAL SCIENCES, 17th Ed., Mack Publishing Co., Easton, Pa. (1990), both of which are incorporated by reference herein in their entirety.

Typical therapeutic doses will be about 0.1 to 1.0 mg/kg of body weight of pure uteroglobin. The does may be adjusted to attain, initially, a blood level of about 0.1 $\mu$M.

A particular formulation of the invention uses a lyophilized form of uteroglobin, in accordance with well known techniques. For instance, 1 to 100 mg of uteroglobin may be lyophilized in individual vials, together with carrier and buffer compound, for instance, such mannitol and sodium phosphate. The uteroglobin may be reconstituted in the vials with bacteriostatic water and then administered, as described elsewhere herein.

Administration regimen

Any effective treatment regimen can be utilized and repeated as necessary to affect treatment.

In clinical practice, the compositions containing uteroglobin or recombinant uteroglobin, alone or in combination with other therapeutic agents are administered in specific cycles until a response is obtained.

For patients who initially present without metastatic disease, uteroglobin-based drugs can be used as an immediate initial therapy prior to surgery and radiation therapy, and as a continuous post-treatment therapy in patients at risk for recurrence or metastasis (based upon high PSA, high Gleason's score, locally extensive disease, and/or pathological evidence of tumor invasion in the surgical specimen). Therapy for these patients aims, for instance, to decrease the escape of potentially metastatic cells from the primary tumor during surgery or radiotherapy, decrease the escape of tumor cells from undetectable residual primary tumor, decrease tumor cell attachment to the interior vessel wall, decrease the migration of tumor cells out of the vessel, and thereby decrease invasion into the interstitial spaces of the distal organ.

For patients who initially present with metastatic disease, uteroglobin-based drugs can be used as a continuous supplement to, or possible as a replacement for hormonal ablation. A goal of therapy for these patients is to slow tumor cell escape from both the untreated primary tumor and from the existing metastatic lesions in order to slow the progressive encroachment of further metastases.

In addition, the invention may be particularly efficacious during post-surgical recovery, where the present compositions and methods may be particularly effective in lessening the chances of recurrence of a tumor engendered by shed cells that cannot be removed by surgical intervention.

Gene therapy

Certain embodiments of the present invention relate to anti-metastatic gene therapy. Gene therapy is a new approach to treatment of diseases. Currently, gene therapy protocols relate to therapy of certain carefully chosen disorders, including certain inherited disorders, a number of aggressively fatal cancers and AIDS. The restricted application of gene therapy to a few disorders reflects concerns about the efficacy, safety and ethical implications of the approach in general, and current techniques in particular. Despite the cautious approach mandated by these concerns, and despite the fact that techniques for carrying out gene therapy are still in an early stage of development, results from the first few trials have been very encouraging, some spectacularly so. It seems certain that gene therapy techniques will improve rapidly and that gene therapies soon will develop into an increasingly important and ubiquitous modality for treating disease. (Reviewed, for instance, in Tolstoshev, *Ann. Rev. Pharm. Toxicol.* 32: 573–596 (1993) and Morgan et al., *Ann. Rev. Biochem.* 62: 191–217 (1993), which are incorporated by reference herein in their entirety).

The delivery of a variety of therapeutic agents clearly will be accomplished by gene therapy techniques. Many of the procedures now in use or under current development for gene therapy may be used in accordance with the present invention to prevent or inhibit metastasis. Additional techniques that will be developed in the future similarly will be found useful in the present invention. The following discussion is illustrative of the use of gene therapy techniques to prevent or inhibit metastasis in accordance with the present invention.

By gene therapy, in the following discussion, generally is meant the use of a polynucleotide, in a cell, to achieve the production of an agent and the delivery of the agent to a tumor in situ, i.e., in a patient, to engender an anti-metastatic effect. The agent may itself be a anti-metastatic agent or it may engender the production of an anti-metastatic agent upon introduction into the patient.

Approaches to genetic therapy currently being developed, which can be used in accordance with this aspect of the invention disclosed herein, often are grouped into two major categories: ex vivo and in vivo techniques.

Ex vivo techniques generally proceed by removing cells from a patient or from a donor, introducing a polynucleotide into the cells, usually selecting and growing out, to the extent possible, cells that have incorporated, and, most often, can express the polynucleotide, and then introducing the selected cells into the patient. Cells that target tumor cells in vivo, including tumor cells that have migrated from primary or secondary tumor sites, generally are preferred in this type of gene therapy.

In addition, as described further below, the polynucleotide may be introduced directly into the patient. The polynucleotide in this case may be introduced systemically or by injection into a tumor site. The polynucleotide may be in the form of DNA or RNA, alone or in a complex, or in a vector, as discussed further below.

The polynucleotide may be in any of a variety of well-known forms, for instance, a DNA, a DNA fragment cloned in a DNA vector, a DNA fragment cloned in DNA vector and encapsidated in a viral capsid.

The polynucleotide may be an RNA or a DNA. More typically it is a DNA. It may include a promoter, enhancer and other cis-acting control regions that provide a desired level and specificity of expression in the cells of a region operably linked thereto that encodes an RNA, such as an anti-sense RNA, or a protein. The polynucleotides may contain several such operably linked control and encoding regions for expression of one or more mRNAs or proteins, or a mixture of the two.

Preferred in this regard are polynucleotides that encode the anti-metastatic agents described herein above. As noted in the foregoing discussion, inhibitors of arachidonic acid release are preferred. Inhibitors of $PLA_2$ activity are particularly preferred. Among $PLA_2$ inhibitors, uteroglobins and lipocortins are particularly preferred, uteroglobins especially, human uteroglobin particularly among uteroglobins.

Muteins and polypeptide analogs of protein inhibitors also are useful in the invention and may be encoded by polynucleotides for gene therapy to inhibit metastasis. In this regard, muteins and polypeptide analogs of the forego-ing preferred embodiments also are preferred in this aspect of the invention.

In addition, peptide mimetics that can be encoded by a polypeptide for synthesis in cells can be used in accordance with this aspect of the invention. Preferred embodiments in this regard those set out above.

The polynucleotide may be introduced into cells either ex vivo or in vivo, including into the tumor in situ. A variety of techniques have been designed to deliver polynucleotides into cells for constitutive or inducible expression, and these routine techniques can be used in gene therapy of the present invention as well. Polynucleotides will be delivered into cells ex vivo using cationic lipids, liposomes or viral vectors. Polynucleotides will be introduced into cells in vivo, including into cells of tumors in situ, using direct or systemic injection. Methods for introducing polynucleotides in this manner can involve direct injection of a polynucleotide, which then generally will be in a composition with a cationic lipid or other compound or compounds that facilitate direct uptake of DNA by cells in vivo. Such compositions may also comprise ingredients that modulate physiological persistence. In addition, polynucleotides can be introduced into cells in vivo in viral vectors.

Genetic therapies in accordance with the present invention may involve a transient (temporary) presence of the gene therapy polynucleotide in the patient or the permanent introduction of a polynucleotide into the patient. In the latter regard, gene therapy may be used to repair a dysfunctional gene to prevent or inhibit metastasis.

Genetic therapies, like the direct administration of agents discussed above, in accordance with the present invention may be used alone or in conjunction with other therapeutic modalities.

Combined with other treatments

Uteroglobin may be used in conjunction with other treatment modalities. Other common treatment modalities are discussed below specifically by reference to prostate cancer. It will be appreciated that similar consideration will apply to treatment of other metastatic cancers. The present invention may be used in conjunction with any current or future therapy.

Surgery and Radiation

In general, surgery and radiation therapy are employed as potentially curative therapies for patients under 70 years of age who present with clinically localized disease and are expected to live at least 10 years. Neither treatment modality has a significant role in the management of metastatic diseases, and neither treatment is generally performed if metastasis is present at initial diagnosis.

Approximately 70% of newly diagnosed prostate cancer patients fall into this category. Approximately 90% of these patients (63% of total patients) undergo surgery, while approximately 10% of these patients (7% of total patients) undergo radiation therapy.

Histopathological examination of surgical specimens reveals that approximately 63% of patients undergoing surgery (40% of total patients) have locally extensive tumors or regional (lymph node) metastasis that was undetected at initial diagnosis. These patients are at a significantly greater risk of recurrence or metastasis. Approximately 40% of these patients will actually develop recurrence or metastasis within 5 years after surgery. Results after treatment with radiation are even less encouraging. Approximately 80% of patients who have undergone radiation as their primary therapy have disease persistence or develop recurrence or metastasis within 5 years after treatment.

Currently, surgical and radiotherapy patients generally do not receive any immediate follow-up therapy. Rather, they typically are monitored for elevated Prostate Specific Antigen ("PSA"), which is the primary indicator of recurrence or metastasis.

Thus, there is considerable opportunity to use the present invention in conjunction with surgical intervention.

Hormonal Therapy

Hormonal ablation is the most effective palliative treatment for the 10% of patients presenting with metastatic disease at initial diagnosis. Hormonal ablation by medication and/or orchiectomy is used to block hormones that support the further growth and metastasis of prostate cancer. With time, both the primary and metastatic tumors of virtually all of these patients become hormone-independent and resistant to therapy. Approximately 50% of patients presenting with metastatic disease die within 3 years after initial diagnosis, and 75% of such patients die within 5 years after diagnosis.

In this regard, it may be worth noting that the natural uteroglobin gene is dependent upon hormones for expression, and hormonal ablation may decrease expression of the endogenous uteroglobin gene, both in tumor cells and in the normal tissue surrounding the tumor. A uteroglobin-deficient state could render the patient more susceptible to successful metastasis. Continuous supplementation with uteroglobin-based drugs may be used to prevent or reverse this potentially metastasis-permissive state from developing in hormonal therapy treatment modalities.

Chemotherapy

Chemotherapy has been more successful with some cancers than with others. It is likely that the combination of chemotherapy with therapies of the present invention in some cases will be synergistic. Chemotherapy currently has little effect on prostate cancer and is used only as a last resort, with universally dismal results.

Immunotherapy

The present invention also can be used in conjunction with immunotherapies. Not only may the methods and compositions herein disclosed be used with the increasing variety of immunological reagents now being tested or used to treat cancer, but it also may be used with those that come into practice in the future. The present invention thus may be used with immunotherapies based on polyclonal or monoclonal antibody-derived reagents, for instance. Monoclonal antibody-based reagents are among those most highly preferred in this regard. Such reagents are well known and are described in, for instance, Ritter MONOCLONAL ANTIBODIES—PRODUCTION, ENGINEERING AND CLINICAL APPLICATIONS, Ritter et al., Eds., Cambridge University Press, Cambridge, UK (1995), which is incorporated by reference herein in its entirety. Radiolabelled monoclonal antibodies for cancer therapy, in particular, also are well known and are described in, for instance, CANCER THERAPY WITH RADIOLABELLED ANTIBODIES, D. M. Goldenberg, Ed., CRC Press, Boca Raton, Fla. (1995), which is incorporated by reference herein in its entirety.

Cryotherapy

Cryotherapy recently has been applied to the treatment of some cancers. Methods and compositions of the present invention also can be used in conjunction with an effective therapy of this type.

Compositions comprising several active agents

According to another aspect of the invention, pharmaceutical compositions of matter useful for inhibiting cancer metastases are provided that contain, in addition to the aforementioned compounds, an additional therapeutic agent. Such agents may be chemotherapeutic agents, ablation or other therapeutic hormones, antineoplastic agents, monoclonal antibodies useful against cancers and angiogenesis inhibitors. The following discussion highlights some agents in this respect, which are illustrative, not limitative. A wide variety of other effective agents also may be used.

Among hormones which may be used in combination with the present invention diethylstilbestrol (DES), leuprolide, flutamide, cyproterone acetate, ketoconazole and amino glutethimide are preferred.

Among antineoplastic and anticancer agents that may be used in combination with the invention 5-fluorouracil, vinblastine sulfate, estramustine phosphate, suramin and strontium-89 are preferred.

Among the monoclonal antibodies that may be used in combination with the invention CYT356 is preferred.

The present invention is further described by reference to the following, illustrative examples.

EXAMPLE 1

Preparation of human uteroglobin by gene expression

Human uteroglobin was purified from $E.\ coli$ cells expressing a full-length cDNA. The methods for obtaining the cDNA, constructing it into a vector for expression in host, expressing the construct and purifying the protein all involve art routine techniques. Such methods are described specifically with regard to human uteroglobin in Singh et al., BBA 950: 329–337 (1988), Mantile et al., J. Biol Chem. 268: 20343–20351 (1993) and Miele et al., J. Biol. Chem. 265: 6427–6435 (1990), which are incorporated by reference herein in their entirety.

Briefly, in the present illustrative example, which followed the techniques set out in the foregoing references, a clone containing a full-length cDNA encoding human uteroglobin in the well known vector pGEM4Z was digested with PstI. (pGEM4Z may be obtained from Promega, Inc. Many other equally suitable vectors also are available commercially.) The digestion freed a 340-base pair fragment containing all of the cDNA and 53 nucleotides of the pGEM4Z polylinker. The fragment was purified by preparative gel electrophoresis in low melting temperature agarose. The purified fragment was ligated into the PstI site of the expression vector pLD101, downstream of an inducible promoter. The ligation and subsequent cloning produced the plasmid pGEL101. This construct was introduced into $E.\ coli$ strain BL21 (DE3) cells for expression of uteroglobin protein.

For expression, bacteria were cultured under routine conditions for $E.\ coli$ growth, and then induced for uteroglobin expression by making the media 0.45 mM in IPTG (isopropyl-1-thio-D-galactopyranoside). After appropriate further incubation to accumulate expressed protein, the cells were collected and then lysed. Uteroglobin was purified from the lysed cells using standard methods of size exclusion and ion exchange chromatography.

EXAMPLE 2

Cells for assays of metastatic potential

The cell lines used in the illustrative embodiments herein discussed are well known and readily available. The four cell lines of the present examples all were derived from human prostate cancer and are of epithelial cell origin. TSU-Prl, DU-145 and PC3-M are androgen-independent. LNCaP is androgen-sensitive.

DU-145 is described in Stone et al., *Int. J. Cancer* 21: 274–281 (1978), which is incorporated herein by reference in its entirety. The cell line is available from a variety of sources including, for instance, the American Type Culture Collection (Rockville, Md.).

LNCaP is described in Horoszewicz et al., *Cancer Res.* 43: 1809–1818 (1983), which is herein incorporated by reference in its entirety. This cell line may be obtained from, for instance, the American Type Culture Collection (Rockville, Md.).

PC3-M is described in Kaighn et al., *Invent:. Urol.* 11:16–23 (1976) which is herein incorporated by reference in its entirety.

TSU-Prl is described in Hzumi et al., *J. Urology* 137:1304–1306 (1987) which is incorporated by reference in its entirety.

Cells of each line were grown and maintained in monolayer culture in αMEM (minimal essential medium) supplemented with glutamine, 10% fetal bovine serum, penicillin (100 units/ml) and streptomycin (100 (g/ml). Cultures were incubated at 37° C. in 5 $CO_2$/95% air. Media was replaced every second day.

EXAMPLE 3

General assay for invasiveness of cells

1. Culture

As described briefly below, invasiveness of cells was assayed by the methods described in Albini et al., *Cancer Research* 47: 3239–3245 (1987), which is incorporated herein by reference in its entirety. Invasiveness assays and other methods for assessing anti-metastatic affects, as discussed herein below are described in Leyton et al., *Cancer Research* 54:3696–3699 (1994) which is incorporated by reference herein in its entirety.

Cells in logarithmic phase were detached from the growth surface by brief exposure to 0.25% trypsin, 0.25% EDTA, collected and centrifuged at 800 X g for 5 min. The pellet was resuspended in SF medium, counted and seeded into 6 mm dishes, $1.5 \times 10^6$ cells per dish. The cells then were incubated for 24 hr in media containing zero, 0.01, 0.1 and 1.0 $\mu$M uteroglobin. After the incubation cells were gently collected using a rubber policeman and assayed for invasiveness.

Fibroblast conditioned media (FCM) served as a chemoattractant to stimulate invasion. It was prepared by culturing proliferating 3T3 cells for 24 hr. in SF medium and then collecting the media, free of cells. The cell free media thus obtained served as FCM.

Invasiveness was measured using a polycarbonate membrane precoated with a reconstituted basement membrane. Well known RBMs are suitable for this purpose. For example, Albini et al., supra describes RBM of the type employed for these experiments.

Assays were performed in blind-well Boyden chambers. The lower compartment of each chamber was filled with 220 $\mu$l of FCM, as chemo-attractant, or 220 $\mu$l serum-free media, as control for basal invasiveness. A polycarbonate membrane (12-$\mu$m pore size), coated with 25 $\mu$g/50 $\mu$l RBM, was placed over the lower compartment. Tumor cells for assay were added to the upper compartment, $3.0 \times 10^5$ cells per well, and the chambers then were incubated at 37° C. for 6 hr.

(Reconstituted basement membrane preparations for use in accordance with the foregoing assay are readily available from numerous commercial suppliers. One suitable example membrane in this regard is "MATRIGEL" sold by Collaborative Biomedical Products of Bedford, Mass.)

2. Quantitation

Invasive activity was measured by the number of cells that penetrated the RBM, as determined by a technique involving crystal violet staining developed for use with the Boyden chamber. The technique, summarized below, is well known and is described, for instance, in Frandson et al., *Fibrinolysis* 6(Supp4): 71–76 (1992), which is incorporated by reference herein in its entirety.

The RBM-coated membrane was removed from each chamber at the end of the incubation period. The filters were pinned down to a wax plate, keeping the surface with the invading cells upward. The cells were stained on the filters with 0.5% crystal violet in 25% methanol for 10 minutes. Then, the filters were rinsed in distilled water, four times or until crystal violet no longer leached into the wash water. After the wash, the surface of each filter that had been in contact with the wax plate was carefully wiped clean with a moist cotton swab, to remove nonmigrating cells. The filters then were placed in a 24-well cluster plate and dried overnight.

Crystal violet in the invading cells on each filter was extracted twice for 10 minutes into 500 $\mu$l aliquots of 0.1M sodium citrate, 50% ethanol. The amount of crystal violet in the extract was analyzed by absorbance at 585 nm, using a standard spectrometer.

3. Analyses

Assays were carried out in triplicate for each data point.

Variance between control and test groups was analyzed for significance using the standard repeated measures test for analysis of variance. P<0.01 generally was considered indicative of a significant effect, with exceptions, as noted elsewhere herein.

EXAMPLE 4

Correlation of optical density with cell counts, and assay of basal invasiveness To calibrate optical density of the crystal violet extracts against the number of migrating cells on filters, cells were counted, seeded at known densities on filters, incubated to allow attachment and washed. One set of a duplicate set of plates was used for cell counting. The other set was used for staining. For counting, cells were released from the filters by mild trypsinization and then counted using an automated cell counter. For staining, after washing, the cells were stained and crystal violet stain then was extracted from the stained cells, as described in EXAMPLE 3. The optical densities of the extracts were measured by standard spectroscopy. The optical density determined for each filter extract was matched with the number of cells attached to its companion filter, as determined by direct counting. These paired data points served to correlate optical density with cell counts. plotted that displayed the In accordance with the foregoing procedure, several densities of DU-145 cells were seeded into the top chamber of the Boyden jars. The jars were set up in pairs, and for each pair dye uptake by the cells was measured on one filter and the number of cells was counted on the other filter, as described above.

The results are shown in Table I, which sets out the number of cells migrating to the lower face of the filters as a function of the number of cells seeded in the upper chamber. The number of cells migrating to the lower filter surface also is set out as a percentage of the total number of cells seeded in the top chamber. The data in the Table are the means of triplicate determinations for each condition, and the indicated variance is the standard error of the mean.

At cell seedings greater than $2 \times 10^5$ approximately 22% of cells invaded the RBM and migrated through the filter in 6 hr. Seeding higher numbers of cells did not increase invasiveness at 6 hr. (Not shown.)

The cells were counted using an automated cell counter, such as the "COULTER MULTISIZER" made by Coulter, Inc. of Hialeah, Fla. By these experiments it was determined that an absorbance of 0.1 units of the crystal violet extract corresponds to approximately 5000 cells that migrated through the filter.

Similar procedures can be applied to calibrate the migration assay for other cells, to employ the assay to measure the therapeutic activity of other compositions of the present invention.

TABLE 1

Relationship between cell invasion and optical absorbance

| Cells seeded ($\times 10^3$) | O.D. units[a] (585 nm) | Cells invading ($\times 10^1$) | Percentage invasion |
|---|---|---|---|
| 100 | 0.60 ± 0.1 | 31.8 ± 0.2 | 31.8 ± 0.2 |
| 200 | 1.50 ± 0.2 | 42.0 ± 2.1 | 21.2 ± 1.0 |
| 300 | 1.20 ± 0.2 | 72.3 ± 2.7 | 23.0 ± 0.4 |

[a] 1 O.D.unit corresponds to approximately 5,000 cells.

Figure 2:
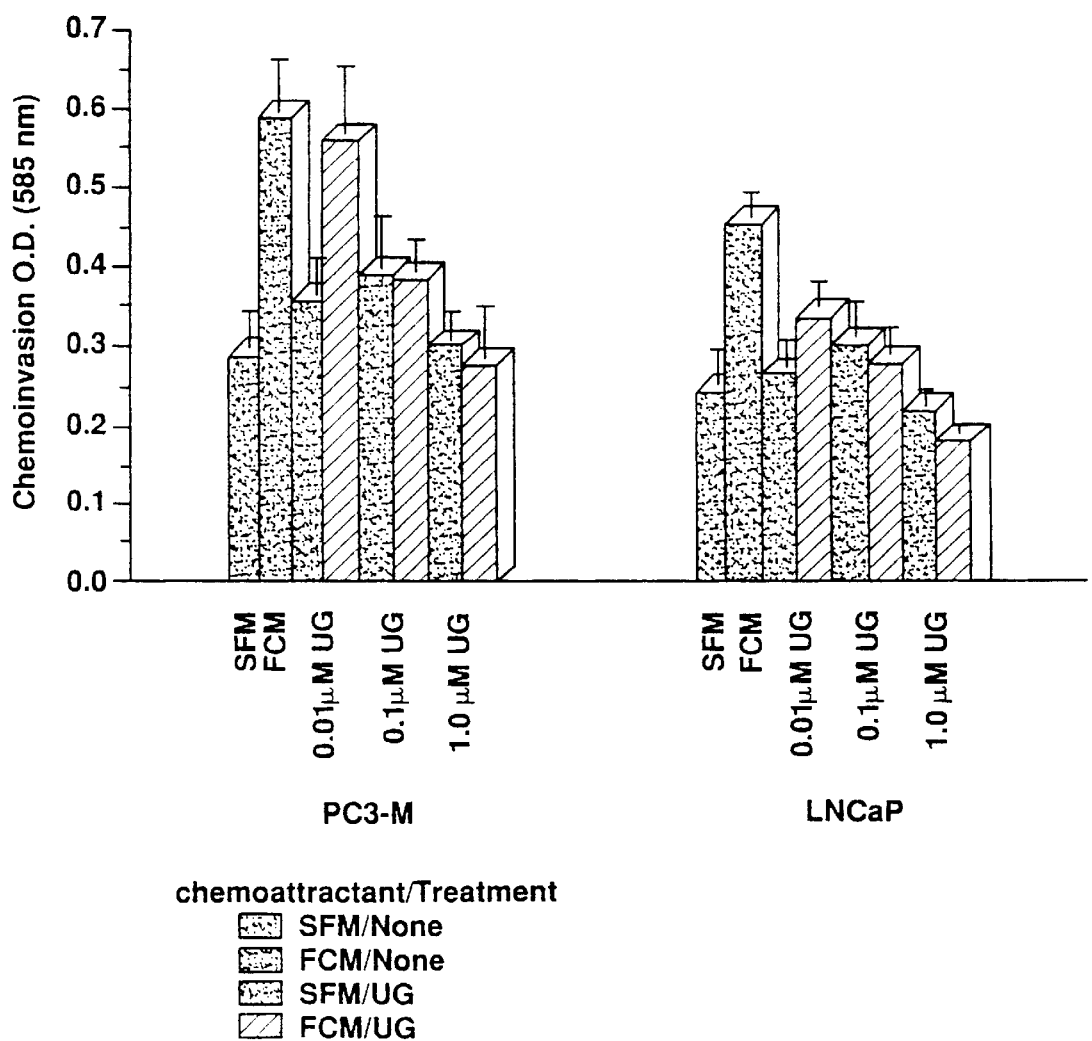
FIG. 2 is a bar chart showing the dose effect of uteroglobin on the invasiveness of cells of the PC3-M and LNCaP cell lines, epithelial cell lines derived from human prostate tumors. LNCaP cells are androgen-sensitive. PC3-M cells are androgen independent. Assays were performed as described in the caption to FIG. 1.

As shown in FIG. 1, cells of the TSU-Prl cell line exhibited the highest rate of basal invasiveness and the highest FCM-stimulated invasiveness. The basal rate for DU-145 cells was 2-fold lower than the rate for TSU-Prl cells, but the rate of stimulated invasiveness was comparable for the two cell lines. As shown in FIG. 2, basal and stimulated invasiveness of PC3-M cells both were 2-fold lower than that observed for DU-145 cells. (N.B. The scale change in FIG. 2.) LNCaP cells exhibited the lowest basal and the lowest stimulated invasiveness. FCM stimulation increased the invasiveness of this cell line 2-3-fold, also as shown in FIG. 2.

EXAMPLE 5

Uteroglobin inhibits invasiveness of tumor cells

The ability of uteroglobin to inhibit tumor cell invasiveness is illustrated by its effect on cell lines treated with 0.01, 0.1 or 1.0 μM uteroglobin. Each of the four cells lines was incubated for 24 hr. with these concentrations of uteroglobin. After the incubation period the cells were rinsed and then assayed for invasiveness. Inhibition of stimulated invasiveness then was quantitatively determined by subtracting the basal invasiveness from FCM-stimulated invasiveness, for each treatment group. Finally, the results were calculated as a percentage of the invasiveness of untreated control cells.

All four cell lines showed a dose-dependent inhibition of FCM-stimulated invasion, as shown in FIGS. 1 and 2, by the bars for FCM/UG. Notably, uteroglobin did not affect basal invasiveness, indicated by the bars labelled SFM/UG. Table 2 shows the average inhibition observed in three independent experiments, each of which was performed in triplicate. The inhibition of invasiveness by uteroglobin was found to be significant at the P<0.01 level for all conditions, except for PC3-M and TSU-Prl cells treated with 0.01 μM uteroglobin, which were significant at the P<0.05 level. As shown in Table 2, 1.0 μM uteroglobin inhibited invasiveness of DU-145 cells by 60%, PC3-M cells by 88%, LNCaP cells by 92% and the TSU-Prl cells by 59%.

TABLE 2

Inhibition of tumor cell invasiveness by uteroglobin
% Inhibition of invasion by uteroglobin

| Cell lines | 0.01 μM | 0.1 μm | 1.0 μM |
|---|---|---|---|
| DU-145 | 45.4 ± 6[a] | 49.9 ± 5[a] | 60.2 ± 11[a] |
| PC3-M | 43.4 ± 15[b] | 82.4 ± 14[a] | 87.9 ± 11[a] |
| TSU-Prl | 33.5 ± 10[b] | 44.4 ± 11[a] | 58.9 ± 8[a] |
| LNCaP | 71.5 ± 10[a] | 81.3 ± 6[a] | 92.3 ± 7[a] |

The table shows that results of assays described herein above. Briefly, tumor cells were cultured in media containing uteroglobin for 24 hr. and then assayed for invasive activity. Basal migration was subtracted and the adjusted measure is expressed as percent of untreated control cells for each cell type. Data is expressed as mean of three independent experiments performed in triplicate, and the variance is the standard error of the mean.
[a]P ≦ 0.001; i.e., statistically significant at the 0.001 level.
[b]P ≦ 0.05; i.e., statistically significant at the 0.05 level.

EXAMPLE 6

Time course of inhibition of invasiveness by uteroglobin

Figure 4:
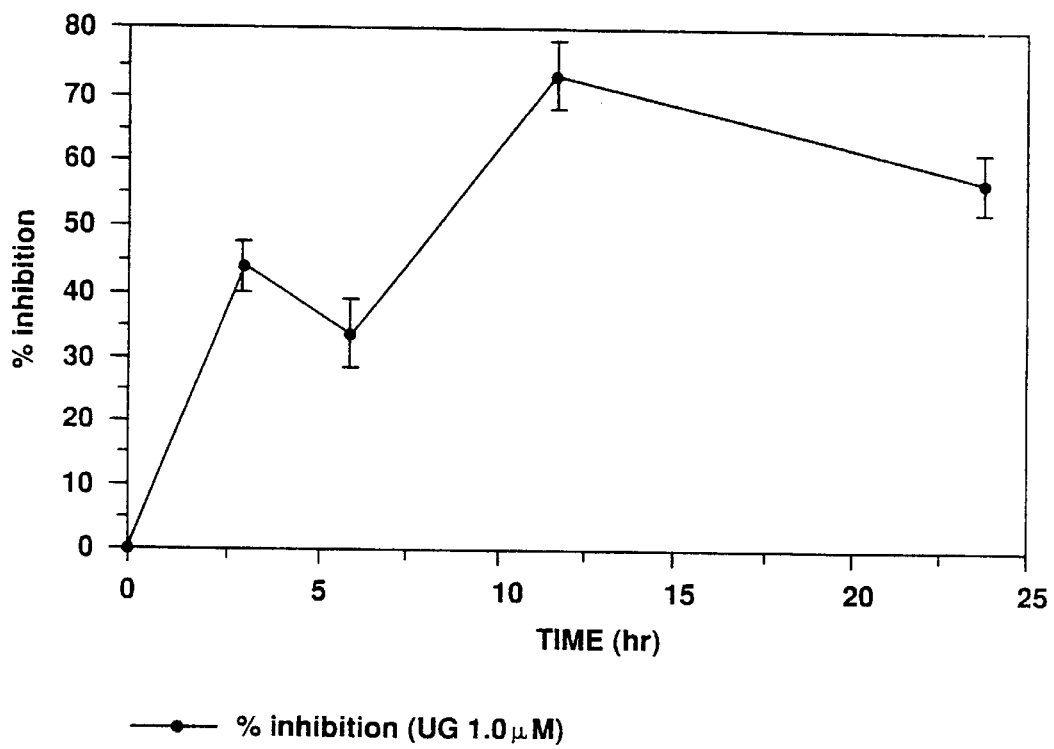
FIG. 4 is a graph showing a time course of the effect of uteroglobin on invasiveness of FCM-stimulated DU-145 cells. Cells were incubated without or with 1.0 $\mu$M uteroglobin for 3, 6, 12, or 24 hr. and then assayed for invasion in response to FCM as described in the caption to FIG. 1.

The time course for suppression of invasiveness of DU-145 cells by uteroglobin was determined over a 24 hr. period. Cells were treated, as described above, for 3, 6, 12, or 24 hr. and then assayed for invasiveness. The maximum inhibition of invasiveness observed in the cells cultured in the presence of uteroglobin was 74%, at 12 hr. 50% maximum inhibition was observed after 3 hr., and at 24 hr. inhibition was 79% of the maximum. FIG. 4 shows these results in graphical form.

EXAMPLE 7

Uteroglobin does not affect simple motility

Experiments carried out to assess motility per se show that uteroglobin does not affect normal cell motility, i.e., migration in the absence of RBM. The results show that uteroglobin specifically inhibits the invasion-associated motility of epithelial tumor cells. Invasion-associated motility, which is implicated more specifically in metastasis than motility per se, involves the synthesis, recruitment, or activation of several different classes of proteolytic enzymes including collagenases, cathepsins, plasminogen activators and a variety of metalloproteinases required for degradation of basement membranes and the ECM. The observation that uteroglobin does not alter cell motility, but inhibits FCM-stimulated invasiveness, indicates that uteroglobin specifically can inhibit metastatic invasiveness without directly altering motility of normal cells. This is an advantageous property for pharmacological intervention where non-specific effects of uteroglobin on normal motility could be disadvantageous.

EXAMPLE 8

Uteroglobin does not affect adhesion to RBM

The anti-invasive activity of uteroglobin is not mediated by an effect on cell adhesion. This can be seen from experiments in which the adhesiveness of DU-145 and PC3-M cells was measured after incubation for 24 hr. in SM media or SM media containing 1.0 μM uteroglobin for 24 hr. Adhesion was tested by removing the incubation media, resuspending the cells in fresh αMEM/SM, counting them, replating the cells and then counting the number of cells that had attached 1, 3 and 6 hr. after replating. The results show that uteroglobin does not alter adhesiveness of the cells. The absence of an effect of uteroglobin on basal migration, illustrated by the results depicted in FIGS. 1 and 2, supports the same conclusion. This is an advantageous property for pharmacological intervention where non-specific effects of uteroglobin on normal cell adhesiveness could be disadvantageous.

EXAMPLE 9

Specificity of uteroglobin anti-metastatic effects

Figure 3:
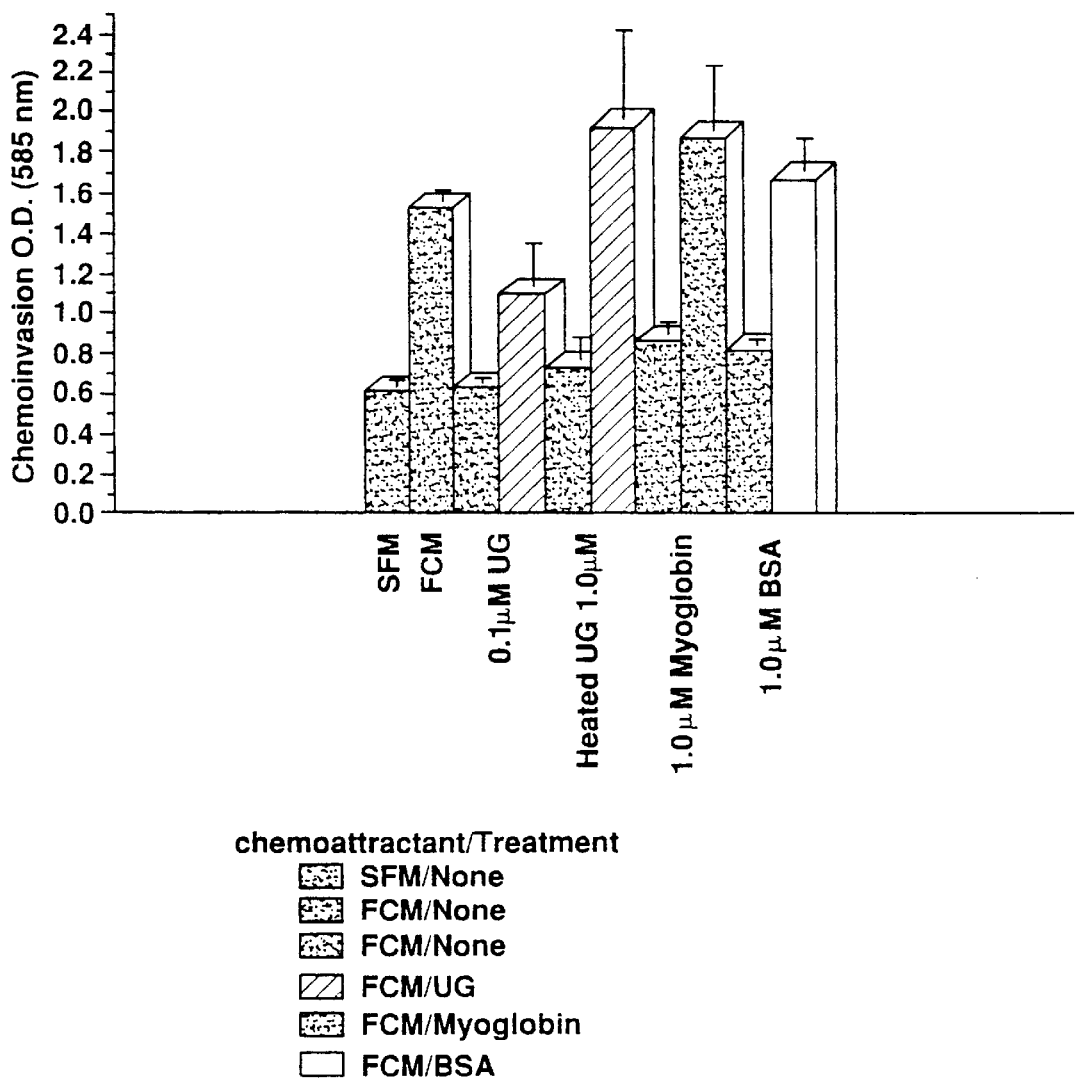
FIG. 3 is a bar chart showing that myoglobin, albumin and heat-inactivated uteroglobin do not affect the invasiveness of DU-145 cells. Assays were performed essentially as described in the caption to FIG. 1.

The specificity of uteroglobin activity was demonstrated in DU-145 cells, using myoglobin, albumin and heat inactivated uteroglobin. Cells were treated for 24 hr with either myoglobin, albumin or uteroglobin that had been inactivated by incubation at 55° C. for 45 min. The results, presented in the graph in FIG. 3, show that myoglobin, albumin and heat-inactivated uteroglobin do not effect invasive activity of tumor cells.

EXAMPLE 10

Uteroglobin inhibits arachidonic acid release by FCM stimulated tumor cells

The effect of uteroglobin on the release of arachidonic acid ("AA") by tumor cells was assayed under conditions of basal and stimulated invasiveness. ($^{14}$C)AA having a specific activity 58.0 mCi/mmol was used to trace the arachidonic acid release. Labelled arachidonic acid of this type can be obtained from several commercial suppliers, such as Amersham, Inc. of Arlington Heights, Ill.

Uteroglobin inhibits release of arachidonic acid by DU-145 cells stimulated by FCM, as shown by the following experiment.

Intracellular arachidonic acid in DU-145 cells was labeled by incubating the cells in media containing $^{14}$C-labelled arachidonic acid. For this purpose approximately 0.75×10$^5$ cells were incubated for 24 hr. at 37° C. in 2 ml of α-MEM/SF media containing 1 μCi of ($^{14}$C)AA. After this, the cells were washed three times with 20 ml 0.2% bovine serum albumin to remove free radioactivity.

The washed, labelled cells were resuspended in 2 ml of α-MEM/SF, FCM or FCM containing 1.0 μM uteroglobin. Cells in each of the three media were incubated at 37° C. and 50 μl aliquots were removed of the media were removed from each culture 0.5, 10, 20 and 30 min., and 1, 2, 3, 4 and 5 hr. after the beginning of the incubation period.

Each aliquot was assayed for AA release, which was measured as $^{14}$C free in the media, determined by scintillation counting. Standard scintillents and counters were used to quantitate radiation emission by $^{14}$C in the samples; e.g., EcoLite Biodegradable scintillant from ICN, Inc.

Stimulation of AA release by FCM was calculated by subtracting the amount of ($^{14}$C)AA released by cells incubated in αMEM/SF media (which was very low) from the amount of ($^{14}$C)AA released by cells incubated in FCM media. The effect of uteroglobin on FCM-stimulated AA release was calculated in the same way, by subtracting the amount of ($^{14}$C)AA released by cells cultured in αMEM/SF from the amount of ($^{14}$C)AA released by cells incubated in FCM containing 1 μM uteroglobin.

As shown in the graph in FIG. 5, arachidonic acid released by cells cultured in FCM media exhibited a biphasic profile. Released AA peaked at 20 min., the peak was followed by a period of reuptake, e.g. 60 min. and then there was a period of sustained release to the end of the 5 hr. incubation period of this experiment.

The presence of 1 μM uteroglobin in FCM media reduced FCM-stimulated release of arachidonic by 77% at 20 min. and 86% at 5 hr.

The dramatic inhibition of release of arachidonic acid by FCM-stimulated tumor cells, together with the foregoing results showing the inhibitory effect of uteroglobin on invasiveness, show that uteroglobin affects an early event in the signalling pathway(s) that control tumor invasiveness.

EXAMPLE 11

A patient presents with metastatic adenocarcinoma of the prostate. The adenocarcinoma appears not to have metastasized. The adenocarcinoma is removed by surgery. Uteroglobin is administered before and after surgery at a dose rate that reaches and then maintains a blood concentration of uteroglobin of approximately 1 μM. After post-operative recovery, the patient is maintained at a decreased level of uteroglobin by a regimen of periodic i.m. self-administration. No further occurrences of the adenocarcinoma develop.

EXAMPLE 12

A patient presents with metastatic adenocarcinoma of the prostate. The adenocarcinoma appears not to have metastasized. The adenocarcinoma is removed by surgery. Uteroglobin is administered before and after surgery, at a dose rate that reaches and then maintains a blood concentration of uteroglobin of approximately 1 μM. After post-operative recovery, the patient is maintained at a decreased level of uteroglobin by intermittent or continuous administration by subdural pump. No further occurrences of the adenocarcinoma develop.

EXAMPLE 13

A patient presents with metastatic adenocarcinoma of the prostate. The adenocarcinoma appears not to have metastasized. The adenocarcinoma is removed by surgery. Uteroglobin is administered before and after surgery, at a dose rate that reaches and then maintains a blood concentration of uteroglobin of approximately 1 μM. After post-operative recovery, the patient is maintained at a decreased level of uteroglobin by intermittent or continuous administration using a transdermal patch. No further occurrences of the adenocarcinoma develop.

EXAMPLE 14

A patient presents with metastatic adenocarcinoma of the prostate. The adenocarcinoma appears to have metastasized, but surgery still is indicated as an effective treatment modality. Tumor tissue is removed by surgery. Uteroglobin is administered from the time, approximately, of the initial diagnosis and continues after surgery, i.m. and i.v., at a dose rate that reaches and then maintains a blood concentration of uteroglobin above 1 μM. After post-operative recovery, the patient is maintained at this level of uteroglobin by a regimen of periodic i.m. self-administration. The patient is monitored carefully for intolerable adverse side-effects of high-dose uteroglobin administration. No further tumors develop.

EXAMPLE 15

A patient presents with metastatic adenocarcinoma of the prostate. The adenocarcinoma appears to have metastasized, but surgery still is indicated as an effective treatment modality. Tumor tissue is removed by surgery. Uteroglobin is administered from the time, approximately, of the initial diagnosis and continues after surgery, i.m. and i.v., at a dose rate that reaches and then maintains a blood concentration of uteroglobin above 1 $\mu$M. After post-operative recovery, the patient is maintained at this level of uteroglobin by a regimen of periodic i.m. self-administration. The patient is monitored carefully for intolerable adverse side-effects of high-dose uteroglobin administration. Although some of the original, small tumorous masses are detected after surgery, they do not grow in size.

EXAMPLE 16

A patient presents with metastatic adenocarcinoma of the prostate. The adenocarcinoma appears to have metastasized, but surgery still is indicated as an effective treatment modality. Tumor tissue is removed by surgery. Uteroglobin is administered from the time, approximately, of the initial diagnosis and continues after surgery, i.m. and i.v., at a dose rate that reaches and then maintains a blood concentration of uteroglobin above 1 $\mu$M. After post-operative recovery, the patient is maintained at this level of uteroglobin by a regimen of periodic i.m. self-administration. The patient is monitored carefully for intolerable adverse side-effects of high-dose uteroglobin administration. Tumorous masses are detected after surgery, but their growth is slowed.

EXAMPLE 17

A patient presents with a tumor of the breast, of epithelial cell origin. The tumor, which appears to be of a metastatic type, appears not to have metastasized. The tumor is removed by surgery. Uteroglobin is administered after surgery, i.m. and i.v., at a dose rate that reaches and then maintains a blood concentration of uteroglobin of approximately 1 $\mu$M. After post-operative recovery, the patient is maintained at a decreased level of uteroglobin by a regimen of periodic i.m. self-administration. No further occurrences of the tumor develop.

EXAMPLE 18

A patient presents with a breast tumor of epithelial cell origin. The breast tumor has metastasized. Numerous secondary tumors are detected. Insofar as possible, tumor tissue is removed by surgery. Surgical intervention is aggressive. Uteroglobin is administered from the time, approximately, of the initial diagnosis and continues after surgery, i.m. and i.v., at a dose rate that reaches and then maintains a blood concentration of uteroglobin above 1 $\mu$M. After post-operative recovery, the patient is maintained at this level of uteroglobin by a regimen of periodic i.m. self-administration. The patient is monitored carefully for intolerable adverse side-effects of high-dose uteroglobin administration. No further tumors develop in the remaining breast or elsewhere in the body.

EXAMPLE 19

Uteroglobin is not expressed or secreted by prostatic adenocarcinoma cells

A 76 year old male underwent radical perineal prostatectomy because of a biopsy-based diagnosis of prostatic adenocarcinoma with a Gleason's score of 4. Postsurgical definitive pathologic diagnosis showed moderately to poorly differentiated adenocarcinoma with a Gleason's score of 8, nodular prostatic hyperplasia, and multifocal high grade prostatic intraepithelial neoplasia (PIN). Perineural and lymphatic invasion was noted, but the seminal vesicles were free of tumor.

With informed consent and in accordance with approved procedures, prostatic tissue was obtained from the diseased prostate gland after removal, for evaluation of uteroglobin expression. Tissue fragments were frozen in liquid nitrogen. Individual slices of frozen tissue were sectioned by cryostat and mounted on silanated microscope slides.

Samples were fixed with 4% formalin for 3 minutes at room temperature and washed for 10 min in phosphate buffered saline (PBS) pH 8.0. Nonspecific reactivity was blocked by incubating samples with rabbit serum (1:100 dilution) for 30 min. The samples were then exposed to a 1:1,000 dilution of goat anti-human uteroglobin primary antibody overnight at 4 degrees C. Control samples were exposed to a 1:100 dilution of goat serum.

All samples were then exposed to biotinylated rabbit anti-goat antibody (1:10,000) for 30 min and then washed with PBS for 10 min. Streptavidin complex was added for 15 min and the samples washed again with PBS for 10 min. DAB was reacted with the samples for 2 min followed by standard staining of the tissue with hematoxylin-eosin.

Slides were analyzed by two certified pathologists, who were not informed of the identity of any slides and who carried out their analyses independently.

In each case, the normal prostatic tissue stained strongly positive for uteroglobin in epithelial cells, especially at the intracellular luminal surface. Stromal cells were negative. Areas of hyperplasia diagnosed independently by both pathologists as PIN stained positively (PIN is considered by some to represent an early pre-neoplastic precursor). In contrast, tumorous epithelial cells exhibited little or no staining for uteroglobin, demonstrating that the tumor cells had lost the ability to synthesize and secrete this protein.

EXAMPLE 20

Uteroglobin mRNA is not detected or is aberrantly processed in cells derived from metastases of human prostatic tumors RNA was isolated from normal prostate tissue and from the DU-145, PC-3 and TSU-PR1 cell lines derived from metastatic human prostate tumors. The RNA was subjected to Northern blotting according to routine and standard procedures, using a radiolabelled uteroglobin cDNA probe. Autoradiographic analysis showed that the normal tissue expresses an abundant normally processed 600 base pair mRNA uteroglobin transcript. In contrast the metastatic tumor cells either did not detectably express the uteroglobin transcript (DU-145 and PC-3) or expressed a grossly aberrant transcript (TSU-PR1).

EXAMPLE 21

A patient presents with urinary obstruction and after digital rectal exam a biopsy of the prostate is taken. The initial presurgical report assigns a Gleason's score of 3 suggesting a low-grade localized tumor. A portion of the biopsy sample is analyzed immunohistochemically for uteroglobin expression which is found to be present in the normal tissue but absent in the tumor cells. The diagnosis, prognosis, and plan for therapy is appropriately altered to reflect the high probability, based on lack of uteroglobin expression, that the tumor is actually of higher grade than initially diagnosed and probably invasive and metastatic. Uteroglobin therapy is immediately begun.

EXAMPLE 22

After radical prostatectomy, a patient presents with high grade metastatic prostatic adenocarcinoma that has become refractory to hormonal therapy. The patient refuses chemotherapy based on its dismal efficacy against prostate cancer and its devastating side effects. In situ hybridization analysis of a tumor biopsy reveals that the uteroglobin gene is not being expressed in the tumor cells. Further analysis of uteroglobin gene structure by SSCP and RFLP indicate the that the gene is mutated and dysfunctional. The patient chooses to become a candidate for gene therapy. The patient is injected with an adenovirus-based plasmid expression vector containing the uteroglobin gene linked to the promotor of the PSA gene which is specifically expressed in prostate cells. The vector is encapsulated in liposomes which have anti-PSA antibody fixed on the surface. The antibody-liposome complex binds specifically to cells secreting PSA which presumably are only the metastatic tumor cells. The liposomes are ingested by the cells and release the plasmids which incorporate into the cells' genomic DNA and begin expressing uteroglobin. The transfected cells expressing uteroglobin reverse their invasive phenotype, thereby ceasing further metastasis and are gradually destroyed by the bodies natural defenses. The metastatic tumors regress and the patient's life is prolonged.

The invention being thus described, it will be obvious that the same may be varied in many ways. Such variations are not to be regarded as a departure from the spirit and scope of the invention and all such modification are intended to be included within the scope of the following claims.

What is claimed is:

1. A kit for identifying prostatic intrapithelial neoplasia, which comprises:

(A) a first reagent that binds specifically to an effector of arachidonic acid release in cells in a biopsy sample prepared for identification of said effector, and (B) a second reagent for detectably labelling said primary binding reagent bound specifically to cells in said biopsy sample, wherein the identification of said effector is diagnostic of said prostatic intraepithelial neoplasia.

2. A kit according to claim 1, wherein said effector is an inhibitor of $PLA_2$.

3. A kit according to claim 2, wherein said inhibitor is uteroglobin.

4. A kit according to claim 1, wherein said first reagent is an antibody.

5. A kit according to claim 4, wherein said effector is an inhibitor of $PLA_2$.

6. A kit according to claim 5, wherein said inhibitor is uteroglobin.

7. A kit according to claim 1, wherein said first reagent is a hybridization probe.

8. A kit according to claim 7, wherein said effector is an inhibitor of $PLA_2$.

9. A kit according to claim 8, wherein said inhibitor is uteroglobin.

* * * * *

UNITED STATES PATENT AND TRADEMARK OFFICE
CERTIFICATE OF CORRECTION

PATENT NO. : 6,054,320
DATED : April 25, 2000
INVENTOR(S) : PATIERNO et al.

It is certified that error appears in the above-indentified patent and that said Letters Patent is hereby corrected as shown below:

Column 38, line 5, after "A kit for identifying prostatic" and before "neoplasia,", please replace "intrapithelial" with --intraepithelial--.

Signed and Sealed this

Sixth Day of February, 2001

Attest:

Q. TODD DICKINSON

*Attesting Officer*                    *Director of Patents and Trademarks*